US009402890B2

(12) United States Patent
Frolov et al.

(10) Patent No.: US 9,402,890 B2
(45) Date of Patent: Aug. 2, 2016

(54) METHODS AND COMPOSITIONS FOR PSEUDOINFECTIOUS ALPHAVIRUSES

(75) Inventors: Ilya Frolov, Birmingham, AL (US); Elena Frolova, Birmingham, AL (US)

(73) Assignee: UAB Research Foundation, Birmingham, AL (US)

( * ) Notice: Subject to any disclaimer, the term of this patent is extended or adjusted under 35 U.S.C. 154(b) by 0 days.

(21) Appl. No.: 13/983,279

(22) PCT Filed: Feb. 1, 2012

(86) PCT No.: PCT/US2012/023444
§ 371 (c)(1),
(2), (4) Date: Nov. 8, 2013

(87) PCT Pub. No.: WO2012/106403
PCT Pub. Date: Aug. 9, 2012

(65) Prior Publication Data
US 2014/0065178 A1    Mar. 6, 2014

Related U.S. Application Data

(60) Provisional application No. 61/438,441, filed on Feb. 1, 2011.

(51) Int. Cl.
*A61K 39/12* (2006.01)
*C07K 14/005* (2006.01)
*C12N 7/00* (2006.01)
*A61K 35/76* (2015.01)
*C07K 14/18* (2006.01)
*C07K 14/08* (2006.01)

(52) U.S. Cl.
CPC ............... *A61K 39/12* (2013.01); *C07K 14/005* (2013.01); *C12N 7/00* (2013.01); *A61K 35/76* (2013.01); *C07K 14/1808* (2013.01); *C12N 2770/36111* (2013.01); *C12N 2770/36121* (2013.01); *C12N 2770/36122* (2013.01); *C12N 2770/36123* (2013.01); *C12N 2770/36134* (2013.01); *G01N 2333/181* (2013.01)

(58) Field of Classification Search
CPC .............. A61K 2039/53; A61K 39/12; A61K 2039/5258; A61K 2039/5254; A61K 2039/55516; A61K 38/162; C07K 14/005; C12N 15/86; C12N 2770/36143; C12N 15/62; C12N 2270/36121; C12N 2770/36162; C12N 2310/351
See application file for complete search history.

(56) References Cited

U.S. PATENT DOCUMENTS

| | | | | |
|---|---|---|---|---|
| 5,843,723 | A * | 12/1998 | Dubensky et al. | 435/69.3 |
| 6,391,632 | B1 * | 5/2002 | Dubensky et al. | 435/325 |
| 6,465,634 | B1 * | 10/2002 | Dubensky et al. | 536/23.72 |
| 6,592,874 | B2 * | 7/2003 | Schlesinger et al. | 424/218.1 |
| 8,093,021 | B2 * | 1/2012 | Hurtado et al. | 435/91.4 |
| 8,748,591 | B2 * | 6/2014 | Weaver et al. | 536/23.72 |
| 2003/0232058 | A1 * | 12/2003 | Dubensky et al. | 424/186.1 |
| 2006/0251678 | A1 * | 11/2006 | Frolov et al. | 424/204.1 |
| 2009/0155301 | A1 * | 6/2009 | Mason et al. | 424/199.1 |
| 2010/0015179 | A1 * | 1/2010 | Frolov et al. | 424/205.1 |
| 2010/0120897 | A1 * | 5/2010 | Hurtado et al. | 514/44 R |
| 2011/0027183 | A1 * | 2/2011 | Mier et al. | 424/9.1 |
| 2011/0207223 | A1 | 8/2011 | Tang et al. | |
| 2011/0207233 | A1 * | 8/2011 | Shimonaka | 436/501 |
| 2014/0170186 | A1 * | 6/2014 | Nabel et al. | 424/218.1 |

OTHER PUBLICATIONS

Hong EM, Perera R, Kuhn RJ. Alphavirus capsid protein helix I controls a checkpoint in nucleocapsid core assembly. J Virol. Sep. 2006;80(18):8848-55.*
Bowie JU, Reidhaar-Olson JF, Lim WA, Sauer RT. Deciphering the message in protein sequences: tolerance to amino acid substitutions. Science. Mar. 16, 1990;247(4948):1306-10.*
Johnson BJ, Kinney RM, Kost CL, Trent DW. Molecular determinants of alphavirus neurovirulence: nucleotide and deduced protein sequence changes during attenuation of Venezuelan equine encephalitis virus. J Gen Virol. Sep. 1986;67 (Pt 9):1951-60.*
Johnson BJ, Kinney RM, Kost CL, Trent DW. VEEV strain TC-83 structural polyprotein. GenBank Acc. No. P05674.1; Dep. Aug. 1, 1992.*
Adams AP, Weaver SC. Structural polyprotein [Venezuelan equine encephalitis virus]. GenBank: ADA84119.1. Dep Jan. 5, 2010.*
Warrier R, Linger BR, Golden BL, Kuhn RJ. Role of sindbis virus capsid protein region II in nucleocapsid core assembly and encapsidation of genomic RNA. J Virol. May 2008;82(9):4461-70. doi: 10.1128/JVI.01936-07. Epub Feb. 27, 2008.*
International Search Report and Written Opinion issued in corresponding PCT Application No. PCT/US2012/023444, mailed Aug. 29, 2012 (15 pages).
Akahata et al. "A VLP vaccine for epidemic Chikungunya virus protects non-human primates against infection" *Nature Medicine* 16(3):334-338 (2010).
Alevizatos et al. "Live, Attenuated Venezuelan Equine Encephalomyelitis Virus Vaccine" *The American Journal of Tropical Medicine and Hygiene* 16(6):762-768 (1967).
Atasheva et al. "Venezuelan Equine Encephalitis Virus Capsid Protein Inhibits Nuclear Import in Mammalian but Not in Mosquito Cells" *Journal of Virology* 82(8):4028-4041 (2008).
Atasheva et al. "Interplay of Acute and Persistent Infections Caused by Venezuelan Equine Encephalitis Virus Encoding Mutated Capsid. Protein" *Journal of Virology* 84(19):10004-10015 (2010).
Atasheva et al. "Venezuelan Equine Encephalitis Virus Capsid Protein Forms a Tetrameric Complex with CRM1 and Importin α/β that Obstructs Nuclear Pore Complex Function" *Journal of Virology* 84(9):4158-4171 (2010).
Atasheva et al. "Pseudoinfectious Venezuelan Equine Encephalitis Virus: a New Means of Alphavirus Attenuation" *Journal of Virology* 87(4):2023-2035 (2013).
Barry et al. "Semliki Forest Virus-Induced Endoplasmic Reticulum Stress Accelerates Apoptotic Death of Mammalian Cells" *Journal of Virology* 84(14):7369-7377 (2010).
Brown et al. "Replication of Alphaviruses in Mosquito Cells" *The Togaviridae and Flaviviridae* Chapter 7:171-207 (1986).

(Continued)

*Primary Examiner* — Rachel B Gill
(74) *Attorney, Agent, or Firm* — Myers Bigel & Sibley, P.A.

(57) ABSTRACT

The present invention provides pseudoinfectious alphavirus particles and methods of making them and using them to produce an immune response to an alphavirus in a subject.

11 Claims, 8 Drawing Sheets

(56) References Cited

OTHER PUBLICATIONS

Burke et al. "Persistence in Humans of Antibody to Subtypes of Venezuelan Equine Encephalomyelitis (VEE) Virus after Immunization with Attenuated (TC-83) VEE Virus Vaccine" *The Journal of Infectious Diseases* 1360):354-359 (1977).

Dal Canto et al. "Central Nervous System Demyelination in Venezuelan Equine Encephalomyelitis Infection" *Journal of the Neurological Sciences* 49:397-418 (1981).

Davis et al. "Attenuating Mutations in the E2 Glycoprotein Gene of Venezuelan Equine Encephalitis Virus: Construction of Single and Multiple Mutants in a Full-Length cDNA Clone" *Virology* 183:20-31 (1991).

Donnelly et al. "DNA Vaccines: Progress and Challenges" *The Journal of Immunology* 175:633-639 (2005).

Elliott et al. "Alphavirus replicon particles encoding the fusion or attachment glycoproteins of respiratory syncytial virus elicit protective immune responses in BALB/c mice and functional serum antibodies in rhesus macaques" *Vaccine* 25(41):7132-7144 (2007).

Forsell et al. "Membrane proteins organize a symmetrical virus" *The EMBO Journal* 19(19):5081-5091 (2000).

Frolov et al. "Alphavirus-based expression vectors: Strategies and applications" *Proceedings of the National Academy of Sciences* 93:11371-11377 (1996).

Frolov et al. "Translation of Sindbis Virus mRNA: Analysis of Sequences Downstream of the Initiating AUG Codon that Enhance Translation" *Journal of Virology* 70(2):1182-1190 (1996).

Frolov et al. "Sindbis Virus Replicons and Sindbis Virus: Assembly of Chimeras and of Particles Deficient in Virus RNA" *Journal of Virology* 71(4):2819-2829 (1997).

Foy et al. "Alphavirus Transducing Systems" *Advances in Experimental Medicine and Biology* 627:19-34 (2008) (Abstract Only).

Garmashova et al. "Analysis of Venezuelan Equine Encephalitis Virus Capsid Protein Function in the Inhibition of Cellular Transcription" *Journal of Virology* 81(24):13552-13565 (2007).

Garmashova et al. "The Old World and New World Alphaviruses Use Different Virus-Specific Proteins for Induction of Transcriptional Shutoff" *Journal of Virology* 81:2472-2484 (2007).

Geigenmller-Gnirke et al. "Deletion Analysis of the Capsid Protein of Sindbis Virus: Identification of the RNA Binding Region" *Journal of Virology* 67:1620-1626 (1993).

Gorchakov et al. "Comparative analysis of the alphavirus-based vectors expressing Rift Valley fever virus glycoproteins" *Virology* 366:212-225 (2007).

Hariharan et al. "DNA Immunization against Herpes Simplex Virus: Enhanced Efficacy Using a Sindbis Virus-Based Vector" *Journal of Virology* 72(2):950-958 (1998).

Kamrud et al. "Development and characterization of promoterless helper RNAs for the production of alphavirus replicon particle" *Journal of General Virology* 91:1723-1727 (2010).

Kinney et al. "The Full-Length Nucleotide Sequences of the Virulent Trinidad Donkey Strain of Venezuelan Equine Encephalitis Virus and its Attenuated Vaccine Derivative, Strain TC-83" *Virology* 170:19-30 (1989).

Konopka et al. "Acute Infection with Venezuelan Equine Encephalitis Virus Replicon Particles Catalyzes a Systemic Antiviral State and Protects from Lethal Virus Challenge" *Journal of Virology* 83(23):12432-12442 (2009).

Leitner et al. "Enhancement of Tumor-specific Immune Response with Plasmid DNA Replicon Vectors" *Cancer Research* 61(1):51-55 (2000).

Lemm et al. "Mutations Which Alter the Level or Structure of nsP4 can Affect the Efficiency of Sindbis Virus Replication in a Host-Dependent Manner" *Journal of Virology* 64(6):3001-3011 (1990).

Liljestrom et al. "In Vitro Mutagenesis of a Full-Length cDNA Clone of Semliki Forest Virus: the Small 6,000-Molecular-Weight Membrane Protein Modulates Virus Release" *Journal of Virology* 65(8):4107-4113 (1991).

Liljestrom, Peter "Alphavirus expression systems" *Current Opinion in Biotechnology* 5(5):495-500 (1994).

Lobue et al. "Alphavirus-Adjuvanted Norovirus-Like Particle Vaccines: Heterologous, Humoral, and Mucosal Immune Responses Protect against Murine Norovirus Challenge" *Journal of Virology* 83(7):3212-3227 (2009).

Ludwig et al. "Comparative Neurovirulence of Attenuated and Non-Attenuated Strains of Venezuelan Equine Encephalitis Virus in Men" *The American Journal of Tropical Medicine and Hygiene* 64(1, 2):49-55 (2001).

Mason et al. "Production and characterization of vaccines based on flaviviruses defective in replication" *Virology* 351(2):432-443 (2006).

Paessler et al. "Recombinant Sindbis/Venezuelan Equine Encephalitis Virus Is Highly Attenuated and Immunogenic" *Journal of Virology* 77(17):9278-9286 (2003).

Pedersen et al. "Isolation of the Vaccine Strain of Venezuelan Equine Encephalomyelitis Virus from Mosquitoes in Louisiana" *American Journal of Epidemiology* 95(5):490-496 (1972).

Perera et al. "Alphavirus Nucleocapsid Protein Contains a Putative Coiled Coil α-Helix Important for Core Assembly" *Journal of Virology* 75(1):1-10 (2001).

Perera et al. "A Heterologous Coiled Coil Can Substitute for Helix I of the Sindbis Virus Capsid Protein" *Journal of Virology* 77(15):8345-8353 (2003).

Phillips et al. "Alphavirus Transducing System: Tools for Visualizing Infection in Mosquito Vectors" *Journal of Visualized Experiments* 45:1-7 (2010).

Pittman et al. "Long-term duration of detectable neutralizing antibodies after administration of live-attenuated VEE vaccine and following booster vaccination with inactivated VEE vaccine" *Vaccine* 14(4):337-343 (1996).

Rumyantsev et al. "Characterization of the RepliVax platform for replication-defective flavivirus vaccines" *Vaccine* 29(32):5184-5194 (2011).

Shustov et al. "Production of Pseudoinfectious Yellow Fever Virus with a Two-Component Genome" *Journal of Virology* 81(21):11737-11748 (2007).

Shustov et al. "Efficient, *trans*-complementing packaging systems for chimeric, Pseudoinfectious dengue 2/yellow fever viruses" *Virology* 400:8-17 (2010).

Smerdou et al. "Two-Helper RNA System for Production of Recombinant Semliki Forest Virus Particles" *Journal of Virology* 73(2):1092-1098 (1999).

Strauss et al. "The Alphaviruses: Gene Expression, Replication, Evolution" *Microbiological Reviews* 58(3):491-562 (1994).

Sviatchenko et al. "The immunogenic properties of a recombinant vaccinia virus with an incorporated DNA copy of the 26S RNA of the Venezuelan equine encephalomyelitis virus" *Voprosy virusologii* 38:222-226 (1993) (Abstract Only).

Thompson et al. "Mucosal and systemic adjuvant activity of alphavirus replicon particles" *Proceedings of the National Academy of Sciences* 103(10):3722-3727 (2006).

Thompson et al. "Alphavirus Replicon Particles Acting as Adjuvants Promote CD8+ T Cell Responses to Co-Delivered Antigen" *Vaccine* 26(33):4267-4275 (2008).

Thompson et al. "The Contribution of Type I Interferon Signaling to Immunity Induced by Alphavirus Replicon Vaccines" *Vaccine* 26(39):4998-5003 (2008).

Volkova et al. "The efficient packaging of Venezuelan equine encephalitis virus-specific RNAs into viral particles is determined by nsP1-3 synthesis" *Virology* 344:315-327 (2006).

Wang et al. "Chimeric Sindbis/Eastern Equine Encephalitis Vaccine Candidates are Highly Attenuated and Immunogenic in Mice" *Vaccine* 25(43):7573-7581 (2007).

Weaver et al. "Evolution of Alphaviruses in the Eastern Equine Encephalomyelitis Complex" *Journal of Virology* 68(1):158-169 (1994).

Weaver et al. "Re-emergence of epidemic Venezuelan equine encephalomyelitis in South America" *The Lancet* 348:436-440 (1996).

Weaver et al. "Transmission Cycles, Host Range, Evolution and Emergence of Arboviral Disease" *Nature Reviews Microbiolggy* 2:789-801 (2004).

(56) References Cited

OTHER PUBLICATIONS

Weiss et al. "Evidence for Specificity in the Encapsidation of Sindbis Virus RNAs" *Journal of Virology* 63(12):5310-5318 (1989).
Weiss et al. "Recombination between Sindbis Virus RNAs" *Journal of Virology* 65(8):4017-4025 (1991).
Zhang et al. "4.4Å cryo-EM structure of an enveloped alphavirus Venezuelan equine encephalitis virus" *The EMBO Journal* 30:3854-3863 (2011).
Notification Concerning Transmittal of International Preliminary Report on Patentability in corresponding PCT Application No. PCT/US2012/023444 mailed Aug. 15, 2013 (8 pages).

* cited by examiner

Fig. 2

```
1                                            40
MFPFQPMYPMQPMPYRNPFAAPRRPWFPRTDPFLAMQVQE
---------------G-------AN----G----------

41                                           80
LTRSMANLTFKQRRDAPPEGPSAKKPKKEASQKQKGGGQG
--------------NN----------SN-GN----A-N-----

81                              conserved  120
KKKKNQGKKKAKTGPPNPKAQNGNKKKTNKKPGKRQRMVM
SGNNN--GGN-S------N-----GNS--AS---------
```

Fig. 3

Protocol 1

Plasmid DNA

↓ RNA synthesis in vitro

VEE PIV genome
— nsP1 | nsP2 | nsP3 | nsP4 — mutC | E2 | E1 —

↓ RNA transfection

Capsid-expressing cells

↓

Release of infectious virions with defective genomes

PIV

↓ Infection of naive cells in vivo or in vitro

↓

Release of subviral particles (SVPs), containing no genetic material

Protocol 2

Plasmid DNA

↓ RNA synthesis in vitro

VEE PIV genome
— nsP1 | nsP2 | nsP3 | nsP4 — mutC | E2 | E1 —

— wt C — Helper RNA encoding RNA packaging-competent capsid

↓ RNA co-transfection

Normal cells

↓

Release of infectious virions with defective genomes

PIV

↓ Infection of naive cells in vivo or in vitro

↓

Release of subviral particles (SVPs), containing no genetic material

VEEV/GFP
—[nsP1|nsP2|nsP3|nsP4]—[GFP]—[C][E2][E1]—

VEEV/RK-/GFP
—[nsP1|nsP2|nsP3|nsP4]—[GFP]—[C][E2][E1]—

—[ ][C]— H/C helper RNA

B)

Fig. 4 (Cont.)
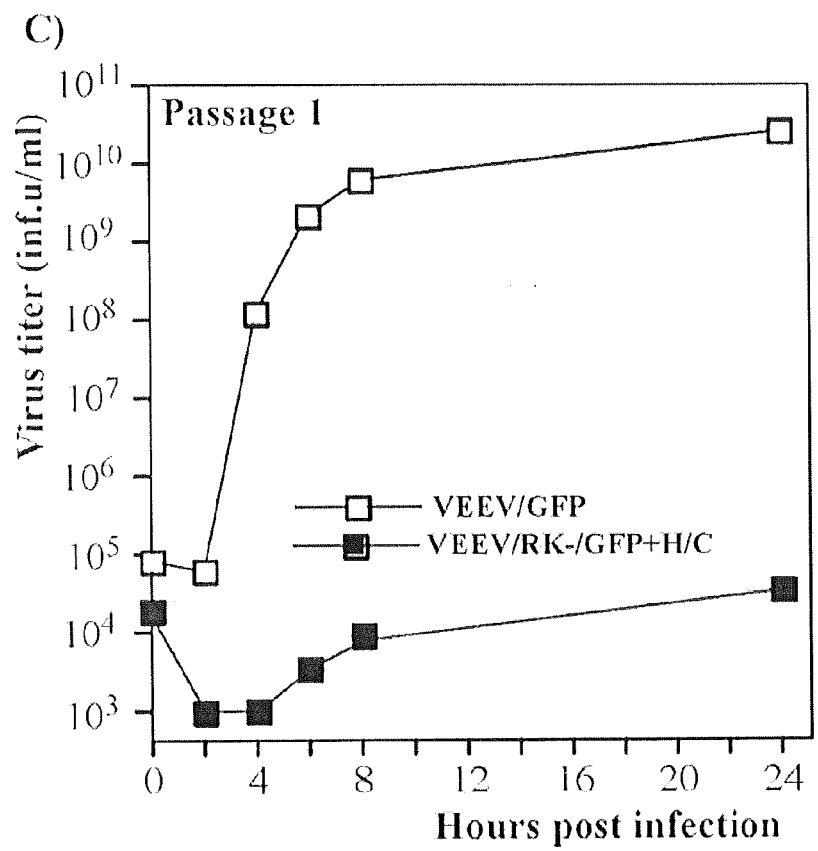
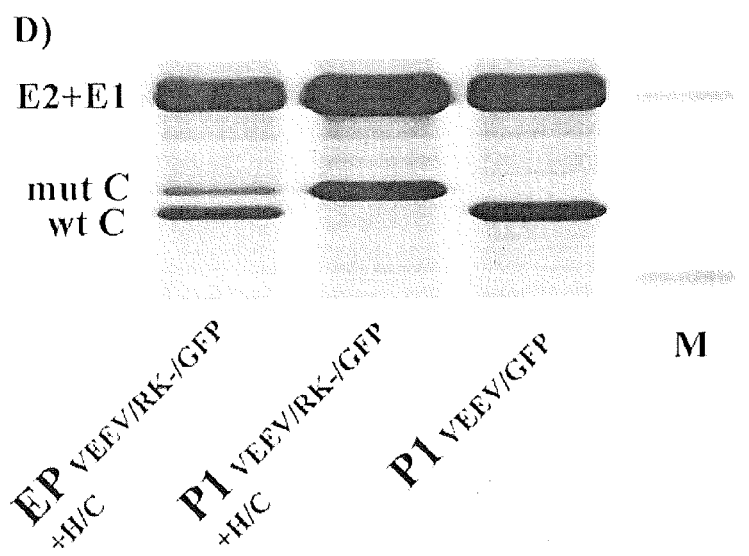

VEEV capsid

+ +++++ Protease

Disordered fragment

Clusters of Arg and Lys

++ Helix I +++++ +++++ CP

NES NLS Conserved peptide

Fig. 6

Amino acid sequence of capsid protein of VEEV TC-83 (which is the same in VEEV TRD):
MFPFQPMYPMQPMPYRNPFAAPRRPWFPRTDPFLAMQVQELTRSMANLTF
KQRRDAPPEGPSAKKPKKEASQKQKGGGQGKKKKNQGKKKAKTGPPNPKA
QNGNKKKTNKKPGKRQRMVMKLESDKTFPIMLEGKINGYACVVGGKLFRP
MHVEGKIDNDVLAALKTKKASKYDLEYADVPQNMRADTFKYTHEKPQGYY
SWHHGAVQYENGRFTVPKGVGAKGDSGRPILDNQGRVVAIVLGGVNEGSR
TALSVVMWNEKGVTVKYTPENCEQW Amino acid sequence of capsid protein of Chikungunya Thai strain:
MEFIPTQTFYNRRYQPRPWTPRSTIQIIRPRPRPQRQAGQLAQLISAVNKLTMRAVPQ
QKPRRNRKNKKQKQKQQAPQNNTNQKKQPPKKKPAQKKKKPGRRERMCMKIEND
CIFEVKHEGKVTGYACLVGDKVMKPAHVKGTIDNADLAKLAFKRSSKYDLECAQIP
VHMKSDASKFTHEKPEGYYNWHHGAVQYSGGRFTIPTGAGKPGDSGRPIFDNKGRV
VAIVLGGANEGARTALSVVTWNKDIVTKITPEGAEEW Amino acid sequence of capsid protein of EEEV North America Florida 93:
MFPYPTLNYPPMAPINPMAYRDPNPPRRRWRPFRPPLAAQIEDLRRSIANLTLKQRAP
NPPAGPPAKRKKPAPSLSLRRKKKRPPPPAKKQKRKPKPGKRQRMCMKLESDKTFPI
MLNGQVNGYACVVGGRVFKPLHVEGRIDNEQLAAIKLKKASIYDLEYGDVPQCMK
SDTLQYTSDKPPGFYNWHHGAVQYENNRFTVPRGVGGKGDSGRPILDNKGRVVAIV
LGGVNEGSRTALSVVTWNQKGVTVKDTPEGSEPW Amino acid sequence of WEEV McMillan strain:
MFPYPQLNFPPVYPTNPMAYRDPNPPRRRWRPFRPPLAAQIEDLRRSIAN
LTFKQRSPNPPPGPPPKKKKSAPKPKPTQPKKKKQQAKKTKRKPKPGKRQRMCMKL
ESDKTFPIMLNGQVNGYACVVGGRLMKPLHVEGKIDNEQLAAVKLKKASMYDLEY
GDVPQNMKSDTLQYTSDKPPGFYNWHHGAVQYENGRFTVPRGVGGKGDSGRPILD
NRGRVVAIVLGGANEGTRTALSVVTWNQKGVTIRDTPEGSEPWS

SEQUENCE LISTING

```
<160> NUMBER OF SEQ ID NOS: 6

<210> SEQ ID NO 1
<211> LENGTH: 120
<212> TYPE: PRT
<213> ORGANISM: Venezuelan equine encephalitis virus

<400> SEQUENCE: 1

Met Phe Pro Phe Gln Pro Met Tyr Pro Met Gln Pro Met Pro Tyr Arg
1               5                   10                  15

Asn Pro Phe Ala Ala Pro Arg Arg Pro Trp Phe Pro Arg Thr Asp Pro
            20                  25                  30

Phe Leu Ala Met Gln Val Gln Glu Leu Thr Arg Ser Met Ala Asn Leu
        35                  40                  45

Thr Phe Lys Gln Arg Arg Asp Ala Pro Pro Glu Gly Pro Ser Ala Lys
    50                  55                  60

Lys Pro Lys Lys Glu Ala Ser Gln Lys Gln Lys Gly Gly Gly Gln Gly
65                  70                  75                  80

Lys Lys Lys Lys Asn Gln Gly Lys Lys Lys Ala Lys Thr Gly Pro Pro
                85                  90                  95

Asn Pro Lys Ala Gln Asn Gly Asn Lys Lys Lys Thr Asn Lys Lys Pro
            100                 105                 110

Gly Lys Arg Gln Arg Met Val Met
        115                 120

<210> SEQ ID NO 2
<211> LENGTH: 275
<212> TYPE: PRT
<213> ORGANISM: Venezuelan equine encephalitis virus
```

```
<400> SEQUENCE: 2

Met Phe Pro Phe Gln Pro Met Tyr Pro Met Gln Pro Met Pro Tyr Arg
1               5                   10                  15

Asn Pro Phe Ala Ala Pro Arg Arg Pro Trp Phe Pro Arg Thr Asp Pro
            20                  25                  30

Phe Leu Ala Met Gln Val Gln Glu Leu Thr Arg Ser Met Ala Asn Leu
        35                  40                  45

Thr Phe Lys Gln Arg Arg Asp Ala Pro Glu Gly Pro Ser Ala Lys
    50                  55                  60

Lys Pro Lys Lys Glu Ala Ser Gln Lys Gln Lys Gly Gly Gln Gly
65                  70                  75                  80

Lys Lys Lys Lys Asn Gln Gly Lys Lys Ala Lys Thr Gly Pro Pro
                85                  90                  95

Asn Pro Lys Ala Gln Asn Gly Asn Lys Lys Thr Asn Lys Lys Pro
            100                 105                 110

Gly Lys Arg Gln Arg Met Val Met Lys Leu Glu Ser Asp Lys Thr Phe
            115                 120                 125

Pro Ile Met Leu Glu Gly Lys Ile Asn Gly Tyr Ala Cys Val Val Gly
        130                 135                 140

Gly Lys Leu Phe Arg Pro Met His Val Glu Gly Lys Ile Asp Asn Asp
145                 150                 155                 160

Val Leu Ala Ala Leu Lys Thr Lys Lys Ala Ser Lys Tyr Asp Leu Glu
                165                 170                 175

Tyr Ala Asp Val Pro Gln Asn Met Arg Ala Asp Thr Phe Lys Tyr Thr
            180                 185                 190

His Glu Lys Pro Gln Gly Tyr Tyr Ser Trp His His Gly Ala Val Gln
        195                 200                 205

Tyr Glu Asn Gly Arg Phe Thr Val Pro Lys Gly Val Gly Ala Lys Gly
    210                 215                 220

Asp Ser Gly Arg Pro Ile Leu Asp Asn Gln Gly Arg Val Val Ala Ile
225                 230                 235                 240

Val Leu Gly Gly Val Asn Glu Gly Ser Arg Thr Ala Leu Ser Val Val
                245                 250                 255

Met Trp Asn Glu Lys Gly Val Thr Val Lys Tyr Thr Pro Glu Asn Cys
            260                 265                 270

Glu Gln Trp
    275

<210> SEQ ID NO 3
<211> LENGTH: 261
<212> TYPE: PRT
<213> ORGANISM: Chikungunya virus

<400> SEQUENCE: 3

Met Glu Phe Ile Pro Thr Gln Thr Phe Tyr Asn Arg Arg Tyr Gln Pro
1               5                   10                  15

Arg Pro Trp Thr Pro Arg Ser Thr Ile Gln Ile Ile Arg Pro Arg Pro
            20                  25                  30

Arg Pro Gln Arg Gln Ala Gly Gln Leu Ala Gln Leu Ile Ser Ala Val
        35                  40                  45

Asn Lys Leu Thr Met Arg Ala Val Pro Gln Gln Lys Pro Arg Arg Asn
    50                  55                  60

Arg Lys Asn Lys Lys Gln Lys Gln Lys Gln Gln Ala Pro Gln Asn Asn
65                  70                  75                  80
```

```
Thr Asn Gln Lys Lys Gln Pro Pro Lys Lys Pro Ala Gln Lys Lys
            85                  90                  95

Lys Lys Pro Gly Arg Arg Glu Arg Met Cys Met Lys Ile Glu Asn Asp
            100                 105                 110

Cys Ile Phe Glu Val Lys His Glu Gly Lys Val Thr Gly Tyr Ala Cys
            115                 120                 125

Leu Val Gly Asp Lys Val Met Lys Pro Ala His Val Lys Gly Thr Ile
            130                 135                 140

Asp Asn Ala Asp Leu Ala Lys Leu Ala Phe Lys Arg Ser Ser Lys Tyr
145                 150                 155                 160

Asp Leu Glu Cys Ala Gln Ile Pro Val His Met Lys Ser Asp Ala Ser
            165                 170                 175

Lys Phe Thr His Glu Lys Pro Glu Gly Tyr Tyr Asn Trp His His Gly
            180                 185                 190

Ala Val Gln Tyr Ser Gly Gly Arg Phe Thr Ile Pro Thr Gly Ala Gly
            195                 200                 205

Lys Pro Gly Asp Ser Gly Arg Pro Ile Phe Asp Asn Lys Gly Arg Val
            210                 215                 220

Val Ala Ile Val Leu Gly Gly Ala Asn Glu Gly Ala Arg Thr Ala Leu
225                 230                 235                 240

Ser Val Val Thr Trp Asn Lys Asp Ile Val Thr Lys Ile Thr Pro Glu
            245                 250                 255

Gly Ala Glu Glu Trp
            260

<210> SEQ ID NO 4
<211> LENGTH: 260
<212> TYPE: PRT
<213> ORGANISM: Eastern equine encephalitis virus

<400> SEQUENCE: 4

Met Phe Pro Tyr Pro Thr Leu Asn Tyr Pro Pro Met Ala Pro Ile Asn
1               5                   10                  15

Pro Met Ala Tyr Arg Asp Pro Asn Pro Pro Arg Arg Arg Trp Arg Pro
            20                  25                  30

Phe Arg Pro Pro Leu Ala Ala Gln Ile Glu Asp Leu Arg Arg Ser Ile
            35                  40                  45

Ala Asn Leu Thr Leu Lys Gln Arg Ala Pro Asn Pro Pro Ala Gly Pro
            50                  55                  60

Pro Ala Lys Arg Lys Lys Pro Ala Pro Ser Leu Ser Leu Arg Arg Lys
65                  70                  75                  80

Lys Lys Arg Pro Pro Pro Ala Lys Lys Gln Lys Arg Lys Pro Lys
            85                  90                  95

Pro Gly Lys Arg Gln Arg Met Cys Met Lys Leu Glu Ser Asp Lys Thr
            100                 105                 110

Phe Pro Ile Met Leu Asn Gly Gln Val Asn Gly Tyr Ala Cys Val Val
            115                 120                 125

Gly Gly Arg Val Phe Lys Pro Leu His Val Glu Gly Arg Ile Asp Asn
            130                 135                 140

Glu Gln Leu Ala Ala Ile Lys Leu Lys Lys Ala Ser Ile Tyr Asp Leu
145                 150                 155                 160

Glu Tyr Gly Asp Val Pro Gln Cys Met Lys Ser Asp Thr Leu Gln Tyr
            165                 170                 175

Thr Ser Asp Lys Pro Pro Gly Phe Tyr Asn Trp His His Gly Ala Val
            180                 185                 190
```

Gln Tyr Glu Asn Asn Arg Phe Thr Val Pro Arg Gly Val Gly Gly Lys
        195                 200                 205

Gly Asp Ser Gly Arg Pro Ile Leu Asp Asn Lys Gly Arg Val Val Ala
210                 215                 220

Ile Val Leu Gly Gly Val Asn Glu Gly Ser Arg Thr Ala Leu Ser Val
225                 230                 235                 240

Val Thr Trp Asn Gln Lys Gly Val Thr Val Lys Asp Thr Pro Glu Gly
            245                 250                 255

Ser Glu Pro Trp
            260

<210> SEQ ID NO 5
<211> LENGTH: 260
<212> TYPE: PRT
<213> ORGANISM: Western equine encephalitis virus

<400> SEQUENCE: 5

Met Phe Pro Tyr Pro Gln Leu Asn Phe Pro Val Tyr Pro Thr Asn
1               5                   10                  15

Pro Met Ala Tyr Arg Asp Pro Asn Pro Pro Arg Arg Arg Trp Arg Pro
                20                  25                  30

Phe Arg Pro Pro Leu Ala Ala Gln Ile Glu Asp Leu Arg Arg Ser Ile
            35                  40                  45

Ala Asn Leu Thr Phe Lys Gln Arg Ser Pro Asn Pro Pro Gly Pro
        50                  55                  60

Pro Pro Lys Lys Lys Lys Ser Ala Pro Lys Pro Lys Pro Thr Gln Pro
65                  70                  75                  80

Lys Lys Lys Lys Gln Gln Ala Lys Lys Thr Lys Arg Lys Pro Lys Pro
                85                  90                  95

Gly Lys Arg Gln Arg Met Cys Met Lys Leu Glu Ser Asp Lys Thr Phe
            100                 105                 110

Pro Ile Met Leu Asn Gly Gln Val Asn Gly Tyr Ala Cys Val Val Gly
        115                 120                 125

Gly Arg Leu Met Lys Pro Leu His Val Glu Gly Lys Ile Asp Asn Glu
    130                 135                 140

Gln Leu Ala Ala Val Lys Leu Lys Lys Ala Ser Met Tyr Asp Leu Glu
145                 150                 155                 160

Tyr Gly Asp Val Pro Gln Asn Met Lys Ser Asp Thr Leu Gln Tyr Thr
                165                 170                 175

Ser Asp Lys Pro Pro Gly Phe Tyr Asn Trp His His Gly Ala Val Gln
            180                 185                 190

Tyr Glu Asn Gly Arg Phe Thr Val Pro Arg Gly Val Gly Gly Lys Gly
        195                 200                 205

Asp Ser Gly Arg Pro Ile Leu Asp Asn Arg Gly Arg Val Val Ala Ile
    210                 215                 220

Val Leu Gly Gly Ala Asn Glu Gly Thr Arg Thr Ala Leu Ser Val Val
225                 230                 235                 240

Thr Trp Asn Gln Lys Gly Val Thr Ile Arg Asp Thr Pro Glu Gly Ser
                245                 250                 255

Glu Pro Trp Ser
            260

<210> SEQ ID NO 6
<211> LENGTH: 120
<212> TYPE: PRT

```
<213> ORGANISM: Artificial
<220> FEATURE:
<223> OTHER INFORMATION: RK- mutant capsid sequence

<400> SEQUENCE: 6

Met Phe Pro Phe Gln Pro Met Tyr Pro Met Gln Pro Met Pro Tyr Gly
1               5                   10                  15

Asn Pro Phe Ala Ala Pro Ala Asn Pro Trp Phe Pro Gly Thr Asp Pro
            20                  25                  30

Phe Leu Ala Met Gln Val Gln Glu Leu Thr Arg Ser Met Ala Asn Leu
            35                  40                  45

Thr Phe Lys Gln Asn Asn Asp Ala Pro Pro Glu Gly Pro Ser Ala Ser
    50                  55                  60

Asn Pro Gly Asn Glu Ala Ser Gln Ala Gln Asn Gly Gly Gly Gln Gly
65              70                  75                  80

Ser Gly Asn Asn Asn Gln Gly Gly Gly Asn Ala Ser Thr Gly Pro Pro
            85                  90                  95

Asn Pro Asn Ala Gln Asn Gly Asn Gly Asn Ser Thr Asn Ala Ser Pro
            100                 105                 110

Gly Lys Arg Gln Arg Met Val Met
            115                 120
```

METHODS AND COMPOSITIONS FOR PSEUDOINFECTIOUS ALPHAVIRUSES

STATEMENT OF PRIORITY

This application is a 35 U.S.C. §371 national phase application of International Application Serial No. PCT/US2012/023444, filed Feb. 1, 2012, which claims the benefit, under 35 U.S.C. §119(e), of U.S. Provisional Application No. 61/438,441, filed Feb. 1, 2011, the entire contents of each of which are incorporated by reference herein.

STATEMENT OF GOVERNMENT SUPPORT

This invention was made with government support under Grant No. R01AI070207 awarded by the National Institutes of Health. The government has certain rights in the invention.

STATEMENT REGARDING ELECTRONIC FILING OF A SEQUENCE LISTING

A Sequence Listing in ASCII text format, submitted under 37 C.F.R. §1.821, entitled 5656.39TSv2_ST25.txt, 11,961 bytes in size, generated on Dec. 2, 2015 and filed via EFS-Web, is provided in lieu of a paper copy. This Sequence Listing is hereby incorporated by reference into the specification for its disclosures.

FIELD OF THE INVENTION

The present invention relates to pseudoinfectious alphavirus particles and their use in eliciting an immune response to an alphavirus in a subject.

BACKGROUND OF THE INVENTION

Of all the disease preventative measures devised to date, excluding the sanitation of water, vaccine development has made the greatest contribution to human health. Most of the currently available live attenuated vaccines (LAVs) were developed by serial passage of viruses in tissue culture or chicken embryos, and their attenuated phenotype relies on a very limited number of point mutations, which mainly accumulate in the structural genes. Thus, LAVs induce strong, protective, long-lived immune responses, characterized by a balanced combination of circulating neutralizing antibodies and cellular immunity. However, they demonstrate residual reactogenicity and their reversion to a more pathogenic phenotype during vaccination remains a strong possibility. Inactivated (INVs) and subunit viral vaccines, on the other hand, demonstrate high safety, but induce cellular immunity very inefficiently. They typically require multiple doses to achieve protective immunity, as well as frequent boosters, making the vaccination process lengthy and expensive. In some cases, preparation of samples prior to chemical inactivation also requires high biocontainment conditions.

Venezuelan equine encephalitis virus (VEEV), eastern equine encephalitis virus (EEEV), western equine encephalitis virus (WEEV), chikungunya virus and various other alphaviruses represent a serious public health threat. They continuously circulate in different parts of the world, including South America, Central America and North America. VEEV has a strong potential for use by terrorists and as biological warfare agent. It has been weaponized and can be applied either alone or in combination with other pathogens. VEEV is classified as a category B, select agent. A need still exists for effective antivirals or vaccines against VEEV and other alphavirus infections.

The present invention overcomes previous shortcomings in the art by providing pseudoinfectious alphaviruses (PIV), combining the efficiency of live attenuated vaccines (LAVs), which results from the ability of the PIV genome to replicate and produce subviral particles (SVPs), with the safety of inactivated (INV) viral vaccines, due to the inability of PIV to develop a spreading infection.

SUMMARY OF THE INVENTION

In one aspect, the present invention provides a pseudoinfectious alphavirus particle comprising a genome encoding: a) alphavirus nonstructural proteins nsP1-4, b) alphavirus structural proteins E2 and E1, and c) an alphavirus capsid protein mutated at one or more positively charged amino acids in the RNA binding domain, whereby binding of RNA to the capsid protein is substantially diminished or eliminated, thereby resulting in production of a noninfectious subviral particle lacking genetic material.

In a further aspect, the present invention provides a noninfectious subviral particle, comprising alphavirus structural proteins E2 and E1 and an alphavirus capsid protein mutated at one or more positively charged amino acids in the RNA binding domain, and lacking genetic material.

Additionally provided herein is a method of eliciting an immune response in a subject, comprising administering to the subject an immunogenic amount of a pseudoinfectious alphavirus of this invention.

Further aspects of this invention include a method of treating and/or preventing an alphavirus infection in a subject, comprising administering to the subject an immunogenic amount of pseudoinfectious alphavirus of this invention.

Also provided herein is a method of producing pseudoinfectious alphavirus particles in cell culture, comprising introducing into an alphavirus permissive cell: a) a nucleic acid molecule encoding: i) alphavirus nonstructural proteins nsP1-4, ii) alphavirus structural proteins E2 and E1, and iii) an alphavirus capsid protein mutated at one or more positively charged amino acids in the RNA binding domain; and b) a helper nucleic acid molecule encoding alphavirus RNA-binding competent capsid protein; and maintaining the cell in culture to produce the pseudoinfectious alphavirus particles.

The present invention further provides a method of producing pseudoinfectious alphavirus particles in cell culture, comprising introducing a nucleic acid molecule encoding: i) alphavirus nonstructural proteins nsp1-4, ii) alphavirus structural proteins E2 and E1, and iii) an alphavirus capsid protein mutated at one or more positively charged amino acids in the RNA binding domain, into an alphavirus permissive cell containing a nucleic acid molecule encoding alphavirus RNA-binding competent capsid protein; and maintaining the cell in culture to produce the pseudoinfectious alphavirus particles.

Furthermore, the present invention provides a population of alphavirus particles comprising the pseudoinfectious alphavirus particles produced by a method of this invention.

BRIEF DESCRIPTION OF THE DRAWINGS

FIG. 2. Alignment of the amino terminal sequence of VEEV capsid (SEQ ID NO:1) and its RK⁻ mutant (SEQ ID NO:6). Sequence involved in capsid dimerization during nucleocapsid formation encompasses amino acids 38-52. NLS sequence involved in its nuclear function and inhibition of cellular transcription encompasses amino acids 64-68. The latter mutations in NLS make capsid and virus noncytopathic and incapable of inhibiting the innate immune response.

FIG. 3. Schematic representation of VEEV PIV genome, its in vitro synthesis, packaging into infectious viral particles using either a capsid-producing cell line or helper RNA, and production of subviral particles. The latter particles are released by the cells infected by PIV.

FIGS. 4A-E. (A) Schematic representation of wt, mutant virus and helper genomes. (B) Release of infectious virus particles from cells transfected with in vitro-synthesized viral RNAs (i.e., from DNA) and VEEV/RK-GFP+H/C helper RNAs. (C) Release of infectious virus particles from cells infected with VEEV/GFP or VEEV/RK-/GFP+H/C harvested after electroporation (MOI 10). (D) Analyses of viruses pelleted from the samples harvested either after electroporation (EP) or after the next passage (aliquots correspond to 3 ml of harvested medium). (E) Analysis of density of viral particles released to the medium at passage 1, by ultracentrifugation in sucrose density gradient.

FIG. 5. Schematic representation of VEEV capsid-specific domains and other functional peptides. NES indicates nuclear export signal, NLS indicates nuclear import signal and +++ indicates clusters of positively charged amino acids.

FIG. 6. Amino acid sequences of non-limiting exemplary capsid proteins of this invention. VEEV TC-83: SEQ ID NO:2; Chikungunya Thai strain: SEQ ID NO:3; EEEV North America Florida 93: SEQ ID NO:4; WEEV McMillan strain: SEQ ID NO:5.

DETAILED DESCRIPTION OF THE INVENTION

Figure 1:
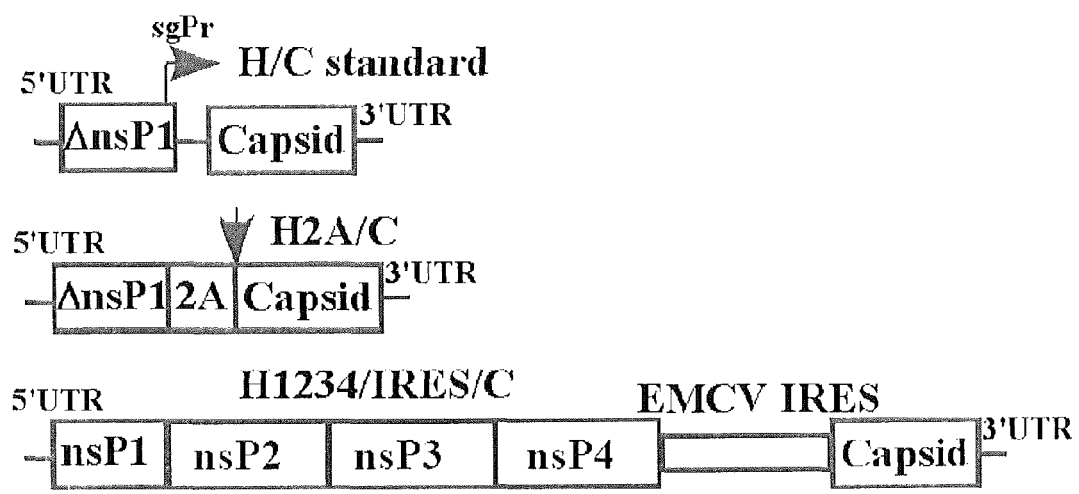
FIG. 1. Schematic representation of helper constructs of this invention: H/C standard (top), H2A/C (middle) and H1234/IRES/C bottom, each encoding an RNA packaging-competent alphavirus capsid protein. H/C standard is a helper with an alphavirus subgenomic promoter. H2A/C is a helper that lacks the subgenomic promoter and does not recombine into replicons or PIV genomes. In H2A/C, 2A is a FMDV 2A protease gene and the vertical arrow shows the FMDV 2A-specific cleavage site. After co-electroporation of the in vitro-synthesized PIV and helper genomes, cells release only PIV genome-containing viral particles. The H1234/IRES/C helper is capable of replicating its own RNA. This latter helper construct is co-electroporated with the PIV genome into cells, and released virions contain both PIV and helper genomes. This two-component genome virus is passaged again and again on naïve cells. The helper construct provides an RNA packaging-competent capsid, and the PIV provides functional glycoproteins. However, both genomes need to be in the same cell. When the multiplicity of infection (MOI) is >1 (which occurs in vitro), infection is productive and spreading. When the MOI is <1 (which occurs in vivo), helper and PIV genomes infect different cells and infection does not spread. No viremia develops, but replicating PIV produces genome-free virions.

As used herein, "a," "an" and "the" can mean one or more than one, depending on the context in which it is used. For example, "a" cell can mean one cell or multiple cells.

Also as used herein, "and/or" refers to and encompasses any and all possible combinations of one or more of the associated listed items, as well as the lack of combinations when interpreted in the alternative ("or").

Furthermore, the term "about," as used herein when referring to a measurable value such as an amount of a compound or agent of this invention, dose, time, temperature, and the like, is meant to encompass variations of ±20%, ±10%, ±5%, ±1%, ±0.5%, or even ±0.1% of the specified amount.

The term "alphavirus structural protein/protein(s)" refers to one or a combination of the structural proteins encoded by alphaviruses. These are produced by the wild type virus as a polyprotein and are described generally in the literature as C-E3-E2-6k-E1. E3 and 6k serve as membrane translocation/transport signals for the two glycoproteins, E2 and E1. Thus, use of the term E1 herein can refer to E1, 6k-E1, or E3-E2-6k-E1, and use of the term E2 herein can refer to E2, E3-E2, E2-6k, PE2, p62 or E3-E2-6k.

The terms "helper," "helper RNA" and "helper construct" are used interchangeably and refer to a nucleic acid molecule (either RNA or DNA) that encodes one or more alphavirus structural proteins. In the present invention, the helper construct generally encodes an RNA-binding competent alphavirus capsid protein. The capsid protein can comprise the amino acid sequence of what is known in the art to be the "wild type" capsid protein of a given alphavirus. Exemplary wild type amino acid sequences of various alphaviruses of this invention are provided herein below. The capsid protein encoded by a helper construct of this invention can also be an alphavirus capsid protein that has the function of binding and packaging alphavirus RNA and may have other modifications that distinguish its amino acid sequence from a wild type sequence, while retaining the RNA binding and packaging function. Optionally, the helper construct of this invention does not comprise a packaging signal. Optionally, the helper construct of this invention can comprise nucleotide sequence encoding all or a portion of one or more alphavirus nonstructural proteins or the helper construct of this invention does not comprise nucleotide sequence encoding all or a portion of one or more alphavirus nonstructural proteins. Further options for the helper construct of this invention can include a helper construct comprising nucleotide sequence encoding all or a portion of one or more alphavirus structural proteins (e.g., in addition to capsid) or the helper construct does not comprise nucleotide sequence encoding one or more alphavirus structural proteins (e.g., besides capsid).

The terms "helper cell" and "packaging cell" are used interchangeably herein and refer to a cell in which alphavirus PIV particles are produced. In particular embodiments, the helper cell or packaging cell of the present invention contains a stably integrated nucleotide sequence encoding an alphavirus RNA-binding competent capsid protein. The helper cell or packaging cell can be any cell that is alphavirus-permissive, i.e., that can produce alphavirus PIV particles upon introduction of a PIV genome. Alphavirus-permissive cells of this invention include, but are not limited to, Vero, baby hamster kidney (BHK), 293, 293T/17 (ATCC accession number CRL-11268), chicken embryo fibroblast (CEF), UMNSAH/DF-1 (ATCC accession number CRL-12203) and Chinese hamster ovary (CHO) cells.

An "isolated cell" as used herein is a cell or population of cells that have been removed from the environment in which the cell occurs naturally and/or altered or modified from the state in which the cell occurs in its natural environment. An isolated cell of this invention can be a cell, for example, in a cell culture. An isolated cell of this invention can also be a cell that can be in an animal and/or introduced into an animal and wherein the cell has been altered or modified, e.g., by the introduction into the cell of an alphavirus PIV particle of this invention.

As used herein, an "alphavirus subgenomic promoter" or "26S promoter" is a promoter as originally defined in a wild type alphavirus genome that directs transcription of a subgenomic messenger RNA as part of the alphavirus replication process. Such a promoter can have a wild type sequence or a sequence that has been modified from wild type sequence but retains promoter activity.

The present invention is based on the unexpected discovery that pseudoinfectious alphavirus particles can infect cells and efficiently produce subviral particles (SVPs), lacking any viral genetic material, which serve as immunogens, without production of a spreading alphavirus infection.

Thus, in one embodiment, the present invention provides a pseudoinfectious alphavirus particle, comprising, consisting essentially of or consisting of, a nucleotide sequence encoding: a) alphavirus nonstructural proteins nsP1-4 (e.g., "wild type" nonstructural proteins or nonstructural proteins lacking mutations that alter the normal function of the nonstructural proteins), b) alphavirus structural proteins E2 and E1 (e.g., "wild type" structural proteins E2 and E1 or structural proteins E2 and E1 lacking mutations that alter the normal function of these structural proteins), and c) an alphavirus capsid protein mutated at one or more positively charged amino acids in the RNA binding domain, whereby binding of RNA to the capsid protein is substantially diminished or eliminated, thereby resulting in production of a noninfectious subviral particle lacking genetic material.

In certain embodiments, a nucleotide sequence of this invention, encoding: a) alphavirus nonstructural proteins nsP1-4 (e.g., "wild type" nonstructural proteins or nonstructural proteins lacking mutations that alter the normal function of the nonstructural proteins), b) alphavirus structural proteins E2 and E1 (e.g., "wild type" structural proteins E2 and E1 or structural proteins E2 and E1 lacking mutations that alter the normal function of these structural proteins), and c) an alphavirus capsid protein mutated at one or more positively charged amino acids in the RNA binding domain, whereby binding of RNA to the capsid protein is substantially diminished or eliminated can be in the form of RNA or DNA.

The present invention further provides a noninfectious subviral particle (SVP), comprising, consisting essentially of or consisting of, alphavirus structural proteins E2 and E1 and an alphavirus capsid protein mutated at one or more positively charged amino acids in the RNA binding domain, and lacking genetic material.

The RNA binding domain in an alphavirus capsid protein comprises about the first 120 amino acids at the amino terminus of the protein. Thus, a pseudoinfectious alphavirus particle of this invention or a noninfectious subviral particle of this invention can comprise a capsid protein that is mutated at one or more positively charged amino acids (e.g., R, K, H, etc. as are well known in the art) within this RNA binding domain. By one or more is meant one, two, three, four, five, six, seven, eight, nine, ten, etc., as would be well understood by one of skill in the art.

For example, in one embodiment, the capsid protein can be mutated at one or more positively charged amino acids between amino acids 15 to 113 (with positively charged amino acids in this region shown in bold) of the amino acid sequence of the capsid protein of VEEV TC-83 strain: MFPFQPMYPM QPMPYRNPFA APRRPWFPRT DPFLAMQVQE LTRSMANLTF KQRRDAPPEG PSAKKPKKEA SQKQKGGGQG KKKKNQGKKK AKT-GPPNPKA QNGNKKKTNK KPGKRQRMVM KLESDK-TFPI MLEGKINGYA CVVGGKLFRP MHVEGKIDND VLAALKTKKA SKYDLEYADV PQNMRADTFK YTHEKPQGYY SWHHGAVQYE NGRFTVPKGV GAKGDSGRPI LDNQGRVVAI VLGGVNEGSR TALSV-VMWNE KGVTVKYTPE NCEQW (SEQ ID NO:2). Thus, a VEEV capsid protein of this invention can be mutated at R16, R23, R24, R29, R53, R54, K64, K65, K67, K68, K73, K75, K81, K82, K83, K84, K88, K89, K90, K92, K99, K105, K106, K107, K110, and/or K111, in any combination (numbering is according to VEEV TC83 capsid protein sequence provided herein).

Thus, the present invention provides a VEEV capsid protein that can be mutated at 1, 2, 3, 4, 5, 6, 7, 8, 9, 10, 11, 12, 13, 14, 15, 16, 17, 18, 19, 20, 21, 22, 23, 24, 25 or 26 positively charged amino acids listed above in any combination, resulting in a capsid protein in which the positive charge in the RNA binding domain has been sufficiently altered to result in a capsid protein in which RNA binding is substantially diminished (e.g., at least about 50%, 60%, 70%, 75%, 80%, 85%, 90%, 95%, 97%, 98%, 99% or more reduction in RNA binding and RNA packaging activity relative to nonmutated capsid protein) or eliminated (100% reduction in binding activity relative to nonmutated capsid protein). Furthermore, these positively charged amino acids of the VEEV capsid protein are shown as mutation sites to produce a capsid protein that lacks RNA binding activity as only one example of this invention and it is to be understood that any one or more of the positively charged amino acids in the RNA binding domain of any other alphavirus (e.g., about the first 100, 110, 120, 125, 130, 135, 140 or 150 amino acids) can be mutated for the same purpose, i.e., to alter the positive charge in the RNA binding domain to result in an alphavirus capsid protein in which RNA binding is substantially diminished or eliminated. These positively charged amino acids in alphaviruses other than VEEV will be numbered differently with respect to the amino acid sequence of a capsid protein of any given alphavirus, but one of skill in the art could readily identify which amino acids in the RNA binding domain are positively charged and produce a capsid protein mutated at any of these amino acid sites in any combination and test the resulting mutated capsid protein for RNA binding activity, thereby producing and identifying a capsid protein of this invention. As nonlimiting examples, the amino acid sequence of the capsid protein of Chikungunya Thai strain, EEEV North America Florida 93 strain and WEEV McMillan strain are provided here as FIG. 6.

In a particular embodiment, a VEEV capsid protein of this invention can comprise one or more of the following specific mutations in any combination (numbering is according to VEEV TC-83 capsid protein amino acid sequence provided herein): R16G, R23A, R24N, R29G, R53N, R54N, K64S, K65N, K67G, K68N, K73A, K75N, K81S, K82G, K83N, K84N, K88G, K89G, K9ON, K92S, K99N, K105G, K106N, K107S, K110A, K111S (as shown in FIG. 2). However, these particular mutations are examples of various amino acid substitutions that can be made for these positively charged amino acid residues in the RNA binding domain of an alphavirus capsid protein and it is to be understood that other amino acid substitutions can be made, in any combination, to reduce the positive charge of the RNA binding domain, resulting in an alphavirus capsid protein in which RNA binding activity has been diminished (e.g., substantially diminished) or eliminated. Nonlimiting examples of other amino acids that can be substituted for positively charged amino acids in the capsid protein of this invention include G, S, T, Q, N, V, A, D, E, L and I, in any combination.

The present invention further provides a population of alphavirus particles, comprising, consisting essentially of, or consisting of the pseudoinfectious alphavirus particles of this invention. Also provided herein is a population of subviral particles, comprising, consisting essentially of, or consisting of the noninfectious subviral particles of this invention. In some embodiments, the population of this invention contains no detectable infectious particles as determined by passage on permissive cells in culture and in other embodiments, the population of this invention has no more than 1 infectious particle per $10^5$ $10^6$, $10^7$, $10^8$, or $10^9$ particles, as measured by passage on permissive cells in culture according to methods well known in the art.

Also provided in the present invention are compositions comprising the alphavirus particles of this invention, such as a composition comprising each of the pseudoinfectious alphavirus particles, the noninfectious subviral particles and/or the populations of this invention, in a pharmaceutically acceptable carrier. By "pharmaceutically acceptable" is meant a material that is not biologically or otherwise undesirable, i.e., the material may be administered to a subject along with the selected particles, and/or populations thereof, without causing substantial deleterious biological effects or interacting in a deleterious manner with any of the other components of the composition in which it is contained. The pharmaceutically acceptable carrier is suitable for administration or delivery to humans and other subjects of this invention. The carrier would naturally be selected to minimize any degradation of the active ingredient and to minimize any adverse side effects in the subject, as would be well known to one of skill in the art (see, e.g., *Remington's Pharmaceutical Science*; latest edition). Pharmaceutical formulations, such as vaccines or other immunogenic compositions of the present invention can comprise an immunogenic amount of the PIV particles of this invention, in combination with a pharmaceutically acceptable carrier. Exemplary pharmaceutically acceptable carriers include, but are not limited to, sterile pyrogen-free water and sterile pyrogen-free physiological saline solution.

The capsid protein of this invention can be the capsid protein of any alphavirus that can be employed in the production of the pseudoinfectious alphavirus particles of this invention. Thus, an alphavirus of this invention can be any alphavirus that can be employed in the production of the pseudoinfectious particles of this invention, as would be known to one of skill in the art and an alphavirus of this invention can be any alphavirus against which it is desirable or necessary to produce an immune response in a subject of this invention. Nonlimiting examples of an alphavirus of this invention include VEEV, WEEV, EEEV, Chikungunya virus, o'nyong-nyong virus, Ross River virus, Barmah Forest virus, Everglades, Mucambo, Pixuna, Semliki Forest virus, Middelburg, Getah, Bebaru, Mayaro, Una, Sindbis, Okelbo, Babanki, Fort Morgan, Ndumu and subgroups thereof as are known in the art. The complete genomic sequences, as well as the sequences of the various structural and nonstructural proteins are available in the literature for numerous alphaviruses and include: Sindbis virus genomic sequence (GenBank® Database Accession Nos. J02363, NCBI Accession No. NC_001547), S.A.AR86 genomic sequence (GenBank Accession No. U38305), VEE genomic sequence (GenBank Accession No. L04653, NCBI Accession No. NC_001449), TC-83 vaccine strain of VEE (Kinney R M et al. (1989) *Virology* 170:19-30; with correction noted in Kinney R M et al. (1993) *J. Virol*, 67(3):1269-1277); Girdwood S. A genomic sequence (GenBank Accession No. U38304), Semliki Forest virus genomic sequence (GenBank Accession No. X04129, NCBI Accession No. NC_003215), and the TR339 genomic sequence (Klimstra et al. (1988) *J. Virol.* 72:7357; McKnight et al. (1996) *J. Virol.* 70:1981). These sequences and references are incorporated by reference herein.

A subject of this invention includes, but is not limited to, warm-blooded animals, e.g., humans, non-human primates, horses, cows, cats, dogs, pigs, rats, and mice.

The present invention also provides a method of eliciting or enhancing an immune response to an alphavirus in a subject, comprising administering to the subject an immunogenic amount of a pseudoinfectious alphavirus particle of this invention, a population of this invention and/or a pharmaceutical composition of this invention, thereby eliciting or enhancing an immune response to an alphavirus in the subject.

Also provided herein is a method of treating and/or preventing an alphavirus infection in a subject, comprising administering to the subject an immunogenic amount of a pseudoinfectious alphavirus particle of this invention, a population of this invention and/or a pharmaceutical composition of this invention, thereby treating and/or preventing an alphavirus infection in the subject.

As used herein, "eliciting an immune response," "enhancing an immune response" and "immunizing a subject" includes the development or enhancement, in a subject, of a humoral and/or a cellular immune response to an alphavirus protein of this invention (e.g., an immunogen, an antigen, an immunogenic peptide, and/or one or more epitopes). A "humoral" immune response, as this term is well known in the art, refers to an immune response comprising antibodies, while a "cellular" immune response, as this term is well known in the art, refers to an immune response comprising T-lymphocytes and other white blood cells, especially the immunogen-specific response by HLA-restricted cytolytic T-cells, i.e., "CTLs."

An "immunogenic amount" is an amount of the alphavirus PIV particles in the populations of this invention that is sufficient to elicit or enhance an immune response in a subject to which the population of particles is administered or delivered. An amount of from about $10^4$ to about $10^9$, especially $10^6$ to $10^8$, infectious units, or "IU," as determined by assays well known in the art, per dose is considered suitable, depending upon the age and species of the subject being treated. Administration may be by any suitable means, such as intraperitoneally, intramuscularly, intranasally, intravenously, intradermally (e.g., by a gene gun), intrarectally and/or subcutaneously. The compositions herein may be administered via a skin scarification method, and/or transdermally via a patch or liquid. The compositions can be delivered subdermally in the form of a biodegradable material that releases the compositions over a period of time.

As used herein, "effective amount" refers to an amount of a population or composition or formulation of this invention that is sufficient to produce a desired effect, which can be a therapeutic effect. The effective amount will vary with the age, general condition of the subject, the severity of the condition being treated, the particular agent administered, the duration of the treatment, the nature of any concurrent treatment, the pharmaceutically acceptable carrier used, and like factors within the knowledge and expertise of those skilled in the art. As appropriate, an "effective amount" in any individual case can be determined by one of ordinary skill in the art by reference to the pertinent texts and literature and/or by using routine experimentation. (See, for example, Remington, *The Science And Practice of Pharmacy* (20th ed. 2000)).

Alternatively, pharmaceutical formulations of the present invention may be suitable for administration to the mucous membranes of a subject (e.g., via intranasal administration, buccal administration and/or inhalation). The formulations may be conveniently prepared in unit dosage form and may be prepared by any of the methods well known in the art.

Also, the composition of this invention may be used to infect or be transfected into dendritic cells, which are isolated or grown from a subject's cells, according to methods well known in the art, or onto bulk peripheral blood mononuclear cells (PBMC) or various cell subfractions thereof from a subject.

If ex vivo methods are employed, cells or tissues can be removed and maintained outside the body according to standard protocols well known in the art while the compositions of this invention are introduced into the cells or tissues.

Immunogenic compositions comprising a population of the particles of the present invention may be formulated by any means known in the art. Such compositions, especially vaccines, are typically prepared as injectables, either as liquid solutions or suspensions. Solid forms suitable for solution in, or suspension in, liquid prior to injection may also be prepared. Lyophilized preparations are also suitable.

The active immunogenic ingredients (e.g., the PIV particles) are often mixed with excipients and/or carriers that are pharmaceutically acceptable and/or compatible with the active ingredient. Suitable excipients include but are not limited to sterile water, saline, dextrose, glycerol, ethanol, or the like and combinations thereof, as well as stabilizers, e.g., HSA or other suitable proteins and reducing sugars.

In addition, if desired, the vaccines or immunogenic compositions may contain minor amounts of auxiliary substances such as wetting and/or emulsifying agents, pH buffering agents, and/or adjuvants that enhance the effectiveness of the vaccine or immunogenic composition. Examples of adjuvants which may be effective include but are not limited to: QS-21, Freund's adjuvant (complete and incomplete), aluminum salts (alum), aluminum phosphate, aluminum hydroxide; N-acetyl-muramyl-L-threonyl-D-isoglutamine (thr-MDP); N-acetyl-nor-muramyl-L-alanyl-D-isoglutamine (CGP 11637, referred to as nor-MDP); N-acetylmuramyl-L-alanyl-D-isoglutaminyl-L-alanine-2-(1'-2'-dipalmitoyl-sn-glycero-3-hydroxyphosphoryloxy)-ethylamine (CGP 19835A, referred to as MTP-PE); and RIBI, which contains three components extracted from bacteria, monophosphoryl lipid A, trehalose dimycolate and cell wall skeleton (MPL+TDM+CWS) in a 2% squalene/Tween 80 emulsion.

Additional examples of adjuvants can include, but are not limited to, immunostimulating agents, such as bacterial cell wall components or synthetic molecules, or oligonucleotides (e.g., CpGs) and nucleic acid polymers (both double stranded and single stranded RNA and DNA), which can incorporate alternative backbone moieties, e.g., polyvinyl polymers.

The effectiveness of an adjuvant may be determined by measuring the amount of antibodies or cytotoxic T-cells directed against the immunogenic product of the alphavirus PIV particles resulting from administration of the particle-containing composition in a vaccine formulation that also comprises an adjuvant or combination of adjuvants. Such additional formulations and modes of administration as are known in the art may also be used.

Adjuvants can be combined, either with the compositions of this invention or with other vaccine formulations that can be used in combination with the compositions of this invention.

The compositions of the present invention can also include other medicinal agents, pharmaceutical agents, carriers, and diluents.

The compositions of this invention can be optimized and combined with other vaccination regimens to provide the broadest (i.e., covering all aspects of the immune response, including those features described hereinabove) cellular and humoral responses possible. In certain embodiments, this can include the use of heterologous prime-boost strategies, in which the compositions of this invention are used in combination with a composition comprising one or more of the following: immunogens derived from a pathogen or tumor, recombinant immunogens, naked nucleic acids, nucleic acids formulated with lipid-containing moieties, non-alphavirus vectors (including but not limited to pox vectors, adenoviral vectors, adeno-associated viral vectors, herpes virus vectors, vesicular stomatitis virus vectors, paramyxoviral vectors, parvovirus vectors, papovavirus vectors, retroviral vectors, lentivirus vectors), and other alphavirus vectors.

The immunogenic (or otherwise biologically active) alphavirus particle-containing populations and compositions of this invention are administered in a manner compatible with the dosage formulation, and in such amount as will be prophylactically and/or therapeutically effective. The quantity to be administered, which can generally ne in the range of about $10^4$ to about $10^{10}$ infectious units in a dose (e.g., about $10^4$, about $10^5$, about $10^6$, about $10^7$, about $10^8$, about $10^9$, or about $10^{10}$), depends on the subject to be treated, the route by which the particles are administered or delivered, the immunogenicity of the expression product, the types of effector immune responses desired, and the degree of protection desired. In some embodiments, doses of about $10^6$, about $10^7$, and about $10^8$ infectious units may be particularly effective in human subjects. Effective amounts of the active ingredient required to be administered or delivered may depend on the judgment of the physician, veterinarian or other health practitioner and may be specific for a given subject, but such a determination is within the skill of such a practitioner.

The compositions and formulations of this invention may be given in a single dose or multiple dose schedule. A multiple dose schedule is one in which a primary course of administration may include 1 to 10 or more separate doses, followed by other doses administered at subsequent time intervals as required to maintain and or reinforce the desired effect (e.g., an immune response), e.g., weekly or at 1 to 4 months for a second dose, and if needed, a subsequent dose(s) after several months (e.g., 4 or 6 months)/years.

Efficacy of the treatment methods of this invention can be determined according to well known protocols for determining the outcome of a treatment of a disease or infection of this invention. Determinants of efficacy of treatment, include, but are not limited to, overall survival, disease-free survival, improvement in symptoms, time to progression and/or quality of life, etc., as are well known in the art.

"Treat" or "treating" or "treatment" refers to any type of action that imparts a modulating effect, which, for example, can be a beneficial effect, to a subject afflicted with a disorder, disease or illness, including improvement in the condition of the subject (e.g., in one or more symptoms), delay or reduction in the progression of the condition, delay of the onset of the disorder, disease or illness, and/or change in any of the clinical parameters of a disorder, disease or illness, etc., as would be well known in the art.

The terms "preventing" or "prevent" as used herein refers to the prophylactic administration of the alphavirus PIV particles of this invention to a subject to protect the subject from becoming infected by the alphavirus and/or to reduce the severity of an alphavirus infection in a subject who becomes infected. Such as subject can be a healthy subject for whom prevention of infection by an alphavirus is desirable. The subject can also be at increased risk of becoming infected by an alphavirus and therefore desires and/or is in need of the methods of preventing alphavirus infection provided herein.

Also provided in this invention are methods of producing the pseudoinfectious alphaviruses of this invention, for use in the therapeutic methods described above. These methods of production generally involve the introduction of the PIV genome (with a mutated capsid protein) into a cell in which an RNA-binding competent alphavirus capsid protein is also present and thus available in trans to produce the PIV particles of this invention. The RNA-binding competent capsid protein can be produced as the result of expression of a nucleotide sequence encoding the capsid protein, wherein the nucleotide sequence has been stably integrated into the genome of the cell. In this embodiment, upon introduction of the PIV genome into the cell in which capsid protein is being produced, the structural proteins E2 and E1 are provided, allowing for assembly of the PIV particles that are capable of a single round of infection. In other embodiments, the PIV genome can be introduced into the cell along with a helper construct that encodes an RNA-binding competent alphavirus capsid protein. Thus, the capsid protein is available in trans from the helper construct for assembly of the PIV particles. Numerous helper constructs, both RNA and DNA, are known in the art. Some nonlimiting examples of helper constructs of this invention are described in FIG. 1. Schematics of the steps of producing PIV particles according to these respective embodiments are shown in FIG. 3.

Thus, in one embodiment, the present invention provides a method of producing pseudoinfectious alphavirus particles in cell culture, comprising introducing into an alphavirus permissive cell: a) a nucleic acid molecule encoding: i) alphavirus nonstructural proteins nsP1-4, ii) alphavirus structural proteins E2 and E1, and iii) an alphavirus capsid protein mutated at one or more positively charged amino acids in the RNA binding domain; and b) a helper nucleic acid molecule encoding alphavirus capsid protein, whereby the structural proteins E2, E1 and capsid are produced in the cell; and maintaining the cell in culture to produce the pseudoinfectious alphavirus particles.

In a further embodiment, the present invention provides a method of producing pseudoinfectious alphavirus particles in cell culture, comprising introducing a nucleic acid molecule encoding: i) alphavirus nonstructural proteins nsP 1-4, ii) alphavirus structural proteins E2 and E1, and iii) an alphavirus capsid protein mutated at one or more positively charged amino acids in the RNA binding domain, into a cell containing a nucleic acid molecule encoding alphavirus capsid protein, whereby the structural proteins E2, E1 and capsid are produced in the cell; and maintaining the cell in culture to produce the pseudoinfectious alphavirus particles.

The present invention further provides a population of alphavirus particles comprising the pseudoinfectious alphavirus particles produced by the methods described herein.

It is understood that the foregoing detailed description is given merely by way of illustration and that modifications and variations may be made therein without departing from the spirit and scope of the invention.

EXAMPLES

The Alphavirus genus in the Togaviridae family includes a number of important human and animal pathogens (26). The New World alphaviruses, which include Venezuelan (VEEV), eastern (EEEV) and western equine encephalitis (WEEV) viruses, represent a serious public health threat in the US (53, 68-70). They continuously circulate in the Central, South and North Americas, including the US, and cause periodic, extensive equine epizootics and epidemics of encephalitis among humans with frequent lethal outcomes and neurological sequelae.

The overall mortality rates are <1% (67), 30-80% (66) and 1-5% (52) for human cases of VEE, EEE and WEE, respectively. However, these values can increase following aerosol infection (51). WEEV, EEEV and particularly VEEV have a potential for use by terrorists and as biological warfare agents. They are very "user friendly" compared to many other viral agents. These viruses can replicate to very high titers, approaching $10^{10}$ infectious units/ml, in a wide variety of cell types, remain highly stable in a lyophilized form and are highly infectious by aerosol.

In spite of the continuous public threat, no effective antivirals and/or vaccines have been developed against VEEV, EEEV or WEEV infections (4). There exists an attenuated VEEV TC-83 vaccine strain, developed more than four decades ago by serial passaging of the virulent TrD strain in cell culture (2). TC-83 is currently the only VEEV strain available for vaccination of laboratory workers and military personnel. However, in nearly 40% of people, vaccination results in a disease with the symptoms typical of natural VEEV infection (4). The attenuated phenotype of TC-83 relies on two point mutations, and therefore a strong probability of reversion to a more virulent phenotype during replication in vivo remains a high risk (33), Moreover, VEEV TC-83 can be transmitted by mosquito vectors, making the possibility of reversion even more likely (47). A formalin-inactivated version of the TC-83 vaccine, C-84 (50), requires repeated boosters because the level of induced neutralizing antibodies is low and they persist for only a short time.

Attenuation of the VEEV TrD strain was also achieved by introduction of lethal mutations into the E3/E2 furin cleavage site of an infectious cDNA clone, followed by selection of a second-site suppressor mutation in the E1 glycoprotein (12). This virus is attenuated (63), but clinical trials with this strain have been stopped due to high rates of adverse reactions in volunteers.

The experimental DNA and adenovirus vaccine candidates demonstrate numerous drawbacks, including very low efficiencies in the induction of neutralizing Ab and pre-existing vector immunity. The virus-like particle (VLP)-based vaccines might be promising in terms of safety, but are very expensive and induce only a short-lived Ab response (3).

Therefore, a need for the development of safe and efficient vaccines against these highly pathogenic New and Old World alphaviruses remains a priority. This need became even more evident recently, when the number of confirmed and lethal cases of EEE among humans and horses in Florida, South Carolina, Georgia, Mississippi, Alabama, Michigan and other states dramatically increased.

The invention described herein is based on three important discoveries provided in the studies described herein: i) identification of a conserved sequence in the alphavirus nsP1-coding fragment, which based on these data, appears to function as a universal packaging signal in many alphavirus serogroups during virion assembly; ii) demonstration of the ability of capsid protein containing mutations at the positively charged amino acid sites to very efficiently form virions lacking viral genetic material; and iii) identification of a capsid-specific peptide that functions in the inhibition of nucleocytoplasmic trafficking, induction of transcriptional shutoff and cytopathic effect (CPE) development in the infected cells.

The present invention is thus directed to designing live alphavirus variants possessing a highly attenuated phenotype, but producing virus-specific antigens for induction of immunity efficiently (e.g., in some embodiments, as efficiently as a wild type (wt) virus). The present invention is also directed to the development of variants that are reduced in the ability to induce viremia and in some embodiments do not induce viremia at all. The modifications will not affect viral RNA replication, structural protein production or the ability to produce viral (or virus-like) particles. However, the released in vivo virions will contain no or very low levels of viral genetic material, and as a result, in particular embodiments, will develop no detectable spreading infection in vivo. Thus, the new variants combine the best characteristics of live attenuated vaccine candidates, which are induction of balanced, efficient and long-term immune response and easy propagation in cultured cells, while also matching inactivated or VLP vaccines, in terms of their safety.

The effectiveness of vaccine candidates is largely determined by the availability of a system for their large-scale production in order to be useful to the public. Therefore, a further aspect of this invention is an in vitro trans-complementation-based packaging system for the large-scale packaging of defective viral genomes into infectious viral particles, which facilitates in vivo applications.

Successful trans-complementation systems for packaging of defective flavivirus genomes have been developed (Mason et al. "Production and characterization of vaccines based on flaviviruses defective in replication" *Virology* 351(2):432-43 (2006); Shustov et al. "Efficient, trans-complementing packaging systems for chimeric, pseudoinfectious dengue 2/yellow fever viruses" *Virology* 400(1):8-17 (2010)). These defective flaviviruses are now in pre-clinical trials as vaccine candidates for TBE and JEV (under the trade name of RepliVax).

Although the studies described herein are focused on VEEV, it is to be understood that the mechanisms described herein for making and using VEEV PIV particles are common to all of the alphaviruses. Therefore, the results can be applied to all of the New and Old World alphaviruses, such as, e.g., EEEV and WEEV, CHIKV and o'nyong-nyong virus, among others. These studies provide a balanced combination of basic, mechanistic research of alphavirus genome packaging and particle formation, and application of the results for the development of a fundamentally new type of safe and efficient alphavirus vaccine.

The present invention is directed to the design and development of live, attenuated encephalitogenic RNA$^+$ viruses, which combine the safety of inactivated virus and efficiency of live vaccines. The key elements of this strategy are as follows: A) High safety of the new variants results from the poor efficiency of packaging of viral genome RNA into viral particles during replication in vivo. In some embodiments, the variant will be incapable or almost completely incapable of packaging viral genomes. B) High efficiency of newly designed alphaviruses in the induction of an immune response is based, in part, on eliciting balanced cellular and neutralizing antibody responses. During in vivo replication, these viruses demonstrate high levels of RNA replication and structural protein production. The latter proteins are presented at the plasma membrane and released in the form of immunogenic, virus-like particles (e.g., subviral particles (SVPs)), containing no viral genetic material. However, these viruses induce only a low level viremia or no viremia at all in terms of infectious virus circulation. C) In some embodiments, the attenuated, defective in viral genome packaging phenotype will be irreversible. D) Application of the attenuated viruses as vaccines includes the development of an in vitro system for the large-scale packaging of these mutated genomes into infectious viral particles for their delivery into cells in vivo.

By introducing multiple, rationally designed mutations into alphavirus capsid protein or into newly identified alphavirus universal RNA packaging signal, alphaviruses will be developed that retain high levels of RNA replication, and production of structural proteins which are released in the form of non-infectious, genome-deficient virus-like particles.

IN representative embodiments, these viruses are capable of inducing a balanced combination of cellular immune response and high levels of neutralizing Abs.

Development and Analysis of Pseudoinfectious (PIV) Alphaviruses.

Experiments described herein are directed to the development of prototype, defective, pseudoinfectious alphaviruses (PIV), which can be propagated in tissue culture, but are able to release only genome-free, immunogenic virions in vivo. These studies are directed to the development of a VEEV capsid protein that is incapable of packaging viral genomes but retains the ability to efficiently form nucleocapsids and genome-free viral particles.

Capsid Protein Structure.

VEEV capsid protein is composed of 275 amino acids (Kinney et al. "Nucleotide sequences of the 26S mRNAs of the viruses defining the Venezuelan equine encephalitis antigenic complex" *Am J Trop Med Hyg.* 59(6):952-64 (1998)) and contains a number of sequences playing various roles in virus replication (FIG. 5). It contains two large structural domains (29): i) The highly ordered carboxy terminal domain is located between amino acids 126 and 275 of the VEEV capsid protein. It functions as a self-protease in processing of the structural polyprotein and is required for co- and post-translational cleavage of the capsid protein from p62 (the precursor of E2 glycoprotein). The carboxy terminal domain has also been proposed as a major determinant for assembly of the capsid proteins into icosahedral nucleocapsids. ii) The amino terminal domain (aa 1-126), in contrast to the protease domain, has no defined secondary structure and is highly positively charged. This domain is responsible for binding to viral genomic RNA and packaging it into infectious virions. However, it also has a number of other important functions. It possesses a small alpha helical peptide, Helix I, located between aa 34-52 that functions as a capsid dimerization signal in nucleocapsid assembly (48, 49, 59). The same helix is also a supraphysiological nuclear export signal (supraNES) playing a role in VEEV capsid-specific inhibition of nuclear trafficking (5). Another short sequence (aa 64-68) in VEEV capsid protein is a nuclear export signal (NLS) (5, 6). Supra NES and NLS bind exportin-α/β and importin CRM1 to form a tetrameric complex that blocks the NPC function and nuclear import. This ultimately leads to inhibition of cellular transcription and downregulation of the innate immune response (5, 6). The third important amino acid sequence is a highly conserved peptide (CP) (aa 111-126 in VEEV capsid protein) that has been shown to play a role in the packaging of SINV genomes (65). Mutations in the latter peptide have a strong negative effect on virus titers (measured in infectious units) and packaging of virus-specific RNA.

In Vitro Studies.

In these studies a VEEV capsid protein was designed that is incapable of packaging viral genomes. To achieve this, an extensive mutagenesis of the amino terminal fragment of the VEEV-derived capsid gene was performed and almost all of the arginines and lysines within the 1-110 aa region were mutated to glycine, alanine and/or asparagine. Based on a computer prediction, the introduced 26 mutations did not change the disordered secondary structure of this protein fragment, but dramatically reduced the positive charge of the amino terminal domain of the protein (e.g., by leaving only 7 of 33 positively charged amino acids remaining) and were expected to have a strong negative effect on the capsid protein's ability to bind and package ssRNAs. The only peptides that remained unmodified were the above-described Helix I, required for capsid dimerization and nucleocapsid formation, and the CP peptide.

Figure 4:
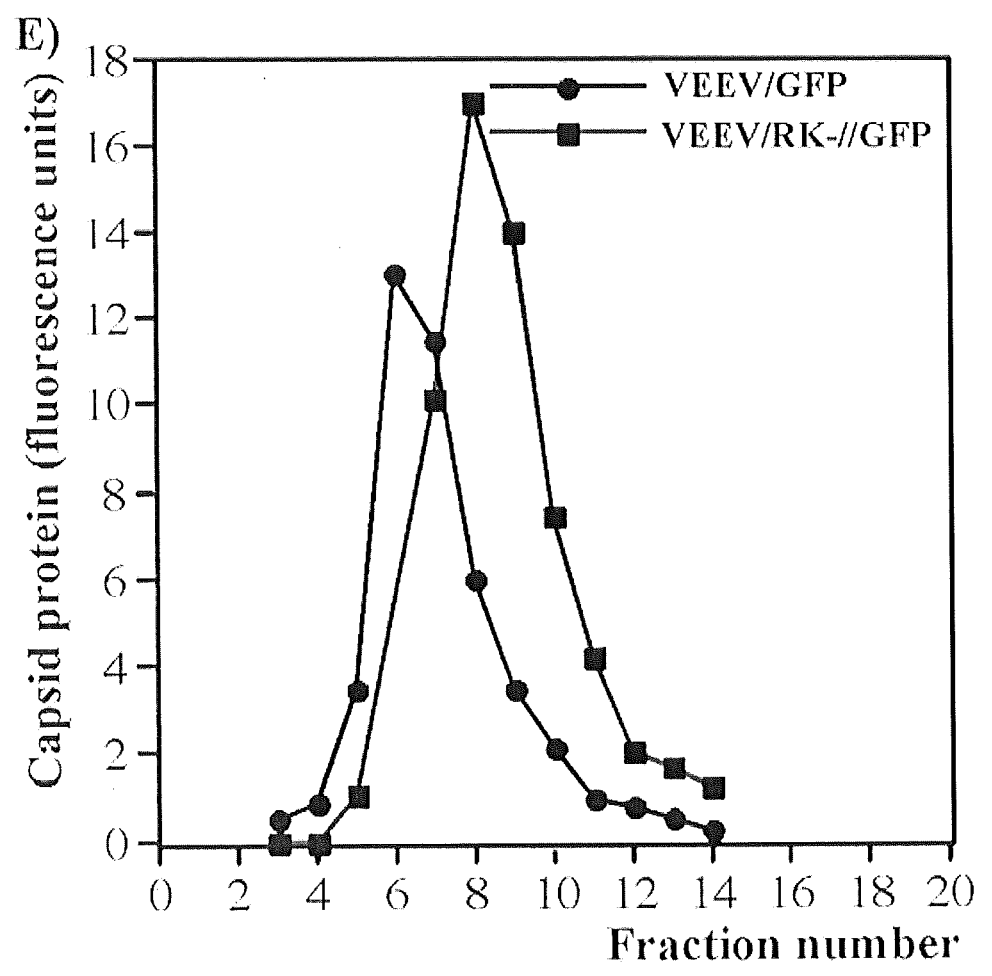

The designed recombinant viral genome (VEEV/RK⁻/GFP) was synthesized in vitro and transfected into BHK-21 cells by electroporation either alone or in the presence of capsid-encoding helper RNA (FIGS. 4A-B). An equal amount of the wt VEEV/GFP RNA was transfected as a positive control. The recombinant capsid mutant did not cause any cytopathic effect (CPE) and released infectious virus to a very low concentration ($\sim 10^4$ infectious units/ml), compared to $10^{10}$ plaque forming units/ml (PFU/ml) of the control VEEV/GFP (FIG. 4B). Thus, each electroporated cell, containing VEEV/GFP genome released ~10,000 infectious viral particles, but only one of 10 cells containing the replicating capsid mutant genome released one infectious virion. This variant was unable to produce plaques, and its titers were determined only based on green fluorescent protein (GFP) fluorescence of the infected cells. Stocks could not be prepared with a concentration above $10^5$ infectious units/ml. Accordingly, at the next passage, due to very low efficiency of infectious virus release, the capsid mutant was unable to develop a productive, spreading infection in tissue culture. However, the inefficient genome packaging by VEEV/RK⁻/GFP capsid could be complemented by supplying the RNA packaging-competent capsid in trans. Co-electroporation of VEEV/RK⁻/GFP and capsid-encoding helper RNA (FIG. 4A) caused a dramatic increase in infectious titers (FIG. 4B), and the released particles contained both wt and mutated capsid protein (FIG. 4D, line 1). Helper RNA was packaged very inefficiently, and at the next passage, cells released VEEV/RK⁻/GFP genome-containing, infectious virions to very low levels (FIG. 4C). However, these cells produced the genome-free viral particles with great efficiency, and the harvested samples contained as many virions as the samples harvested from the VEEV/GFP-infected cells (FIG. 4D, compare lines 2 and 3, which represent viral particles pelleted from 3 ml of media). These infectious virions containing the VEEV/RK⁻/GFP genome are termed "pseudoinfectious virus (PIV)." Particles released from VEEV/RK⁻/GFP-infected cells demonstrated lower density (FIG. 4E), additionally indicating lack of packaged RNA, which correlated with very low infectivity of released virions.

Testing of residual pathogenicity and immunogenicity of the recombinant viruses.

Experimental Design.

To test neurovirulence of the designed, recombinant viruses, 6-days-old NIH-Swiss mice are infected intracerebrally (i.c.) with 20 µl ($10^6$ infectious units) of packaged VEEV/RK⁻ or control VEEV TC-83. At this dose, TC-83, the experimental vaccine, is universally lethal for these mice and, thus, represents a good control for comparative studies. Eight pups are used for each virus, and they are observed for 12 days for any signs of disease, which include development of paralysis and weight loss. If mice develop severe paralysis, they are euthanized. In this scenario, virus titers in their brain tissues are analyzed. In parallel, each day post infection, 3 mice from each group will be euthanized and virus titers in the brains will be assessed for 5 days to evaluate the levels of their replication even if the variants are incapable of causing death.

Testing the Induction of Neutralizing Antibodies and Cellular Immune Response.

Experimental Design.

Groups of 6-week-old NIH Swiss mice (8 mice per group) are infected subcutaneously (s.c.) with $10^5$ and $10^7$ infectious units of packaged VEEV/RK⁻ or control VEEV TC-83. At days 7, 14 and 28 post-infection, blood samples are collected and tested for levels of neutralizing antibodies (Ab) using the PRNT$_{80}$ assay (Wang et al. "Chimeric alphavirus vaccine candidates for chikungunya" *Vaccine* 26(39):5030-9 (2008)), with VEEV TC-83 virus.

In order to assess whether the vaccine constructs elicit cellular immune responses, the total and virus-specific CD4 and CD8 T cell populations are analyzed using a series of established flow cytometry-based assays. The basic approach encompasses infecting separate cohorts of 6-week-old BALB/c mice (6 mice per group) with $10^6$ infectious units of VEEV/mutPS/CmutNLS, packaged VEEV/RK⁻ or control VEEV TC-83. To assess the induction and longevity of the virus-specific T cell responses, PBMC, spleens and lymph nodes are harvested at days 8 (effector phase), 30 (early memory phase) and 60 (memory phase) following infection. First, the global activation of CD4 and CD8 T cells following infection are evaluated by performing polychromatic flow cytometry. Second, the frequencies, phenotypes and functions of the VEEV-specific responses are measured following stimulation of the cell populations infected with tested non-cytopathic viruses or control, uninfected BALB/c cl.7 and A20 cells. The co-culture with the virus-infected stimulators activates any VEEV-specific cells present. This activation is determined by intracellular staining for panels of effector molecules including IFN-g, TNF-a, and IL-2. By using conventional experimental approaches, an assessment can be made of the establishment of effector and memory T cells, their functional quality and whether the candidates induce distinct subsets of memory T cells.

Additional information regarding the protective efficacy of the viruses used is generated in the in vivo CTL assays (21). Taken together, these data provide information about the cellular component of the immune response induced by designed viral mutants. The most favorable result is if a single immunization is sufficient for induction of neutralizing Ab functioning at 1:80 or higher dilutions and induction of cellular immune response at least comparable to that induced by VEEV TC-83. However, if this is not the case, the immune response is boosted with a second immunization 28 days after the first immunization and the assessment of the Ab titers using the PRNT$_{80}$ test and other assays is repeated.

Efficacy Studies in an Animal Model.

Experimental Design.

Constructs selected in the immunological studies are further evaluated in challenge experiments. Groups of 6-week-old NIH Swiss mice (12 mice per group, 2 viruses, 2 doses and a control group) are immunized s.c. with $10^5$ and $10^6$ infectious units of packaged VEEV/RK⁻ PIV. At day 28 post immunization, these mice are infected with 1,000 LD$_{50}$ of VEEV TRD by s.c. route. The same doses are used for challenging sham-immunized mice. Mice are evaluated daily for 12 days for any signs of disease, which include development of paralysis and weight loss. If mice develop severe paralysis, they are euthanized. The same mice are used for the analysis of viremia development. Blood samples are collected by retro-orbital puncture at days 1, 2, 3 and 4 post infection of immunized and unimmunized mice.

As will be understood by one skilled in the art, there are several embodiments and elements for each aspect of the claimed invention, and all combinations of different elements are incorporated herein as embodiments of this invention, so the specific combinations exemplified herein are not to be construed as limitations in the scope of the invention as claimed. If specific elements are removed or added to the group of elements available in a combination, then the group of elements is to be construed as having incorporated such a change.

All references cited herein, including non-patent publications, patent applications, GenBank® Database accession numbers and patents, are incorporated by reference herein in their entireties to the same extent as if each was individually and specifically indicated to be incorporated by reference, and was reproduced in its entirety herein.

REFERENCES

1. Agapov, E. V., I. A. Razumov, I. V. Frolov, A. A. Kolykhalov, S. V. Netesov, and V. B. Loktev. 1994. Localization of four antigenic sites involved in Venezuelan equine encephalomyelitis virus protection. *Arch Virol* 139:173-81.
2. Aguilar, P. V., S. C. Weaver, and C. F. Basler. 2007. Capsid protein of eastern equine encephalitis virus inhibits host cell gene expression. *J Virol* 81:3866-76.
3. Akahata, W., Z. Y. Yang, H. Andersen, S. Sun, H. A. Holdaway, W. P. Kong, M. G. Lewis, S. Higgs, M. G. Rossmann, S. Rao, and G. J. Nabel. A virus-like particle vaccine for epidemic Chikungunya virus protects nonhuman primates against infection, *Nat Med* 16:334-8.
4. Alevizatos, A. C., R. W. McKinney, and R. D. Feigin. 1967. Live, attenuated Venezuelan equine encephalomyelitis virus vaccine. I. Clinical effects in man, *Am J Trop Med Hyg* 16:762-8.
5. Atasheva, S., A. Fish, M. Fornerod, and E. I. Frolova. 2010 Venezuelan Equine Encephalitis Virus Capsid Protein Forms a Tetrameric Complex with CRM1 and Importin alpha/beta that Obstructs Nuclear Pore Complex Function. *J Virol.* 84:4158-4171.
6. Atasheva, S., N. Garmashova, I. Frolov, and E. Frolova. 2008. Venezuelan equine encephalitis virus capsid protein inhibits nuclear import in Mammalian but not in mosquito cells, *J Virol* 82:4028-41.
7. Atasheva, S., V. Krendelchtchikova, A. Liopo, E. Frolova, and I. Frolov. 2010 Interplay of acute and persistent infections caused by Venezuelan equine encephalitis virus encoding mutated capsid protein. *J Virol.* 84:10004-10015.
8. Atasheva, S., E. Wang, A. P. Adams, K. S. Plante, S. Ni, K. Taylor, M. E. Miller, I. Frolov, and S. C. Weaver. 2009. Chimeric alphavirus vaccine candidates protect mice from intranasal challenge with western equine encephalitis virus. *Vaccine* 27:4309-19.
9. Barnes, D., M. Kunitomi, M. Vignuzzi, K. Saksela, and R. Andino. 2008. Harnessing endogenous miRNAs to control virus tissue tropism as a strategy for developing attenuated virus vaccines. *Cell Host Microbe* 4:239-48.
10. Bredenbeek, P. J., I. Frolov, C. M. Rice, and S. Schlesinger. 1993. Sindbis virus expression vectors: Packaging of RNA replicons by using defective helper RNAs. *J. Virol.* 67:6439-6446.
11. Coleman, J. R., D. Papamichail, S. Skiena, B. Futcher, E. Wimmer, and S. Mueller. 2008. Virus attenuation by genome-scale changes in codon pair bias. *Science* 320:1784-7.
12. Davis, N. L., N. Powell, G. F. Greenwald, L. V. Willis, B. J. Johnson, J. F. Smith, and R. E. Johnston. 1991. Attenuating mutations in the E2 glycoprotein gene of Venezuelan equine encephalitis virus: construction of single and multiple mutants in a full-length cDNA clone. *Virology* 183:20-31.
13. Eiring, A. M., J. G. Harb, P. Neviani, C. Garton, J. J. Oaks, R. Spizzo, S. Liu, S. Schwind, R. Santhanam, C. J. Hickey, H. Becker, J. C. Chandler, R. Andino, J. Cortes, P. Hokland, C. S. Huettner, R. Bhatia, D. C. Roy, S. A. Liebhaber, M. A. Caligiuri, G. Marcucci, R. Garzon, C. M. Croce, G. A. Calin, and D. Perrotti. miR-328 functions as an RNA decoy to modulate hnRNP E2 regulation of mRNA translation in leukemic blasts. *Cell* 140:652-65.
14. Fayzulin, R., and I. Frolov. 2004. Changes of the secondary structure of the 5' end of the Sindbis virus genome inhibit virus growth in mosquito cells and lead to accumulation of adaptive mutations. *J Virol* 78:4953-64.
15. Fayzulin, R., R. Gorchakov, O. Petrakova, E. Volkova, and I. Frolov. 2005. Sindbis virus with a tricomponent genome. *J Virol* 79:637-43,
16. Forsell, K., L. Xing, T. Kozlovska, R. H. Cheng, and H. Garoff. 2000. Membrane proteins organize a symmetrical virus. *EMBO J* 19:5081-91.
17. Frolov, I., E. Frolova, and S. Schlesinger. 1997. Sindbis virus replicons and Sindbis virus: assembly of chimeras and of particles deficient in virus RNA. *J Virol* 71:2819-2829.
18. Frolov, I., R. Hardy, and C. M. Rice. 2001. Cis-acting RNA elements at the 5' end of Sindbis virus genome RNA regulate minus- and plus-strand RNA synthesis. *RNA* 7:1638-51.
19. Frolova, E., I. Frolov, and S. Schlesinger. 1997. Packaging signals in alphaviruses. *J Virol* 71:248-58.
20. Frolova, E. I., R. Z. Fayzulin, S. H. Cook, D. E. Griffin, C. M. Rice, and I. Frolov. 2002. Roles of nonstructural protein nsP2 and Alpha/Beta interferons in determining the outcome of Sindbis virus infection. *J Virol* 76:11254-64.
21. Fuller, M. J., A. Khanolkar, A. E. Tebo, and A. J. Zajac. 2004. Maintenance, loss, and resurgence of T cell responses during acute, protracted, and chronic viral infections. *J Immunol* 172:4204-14.
22. Fuller, M. J., and A. J. Zajac. 2003. Ablation of CD8 and CD4 T cell responses by high viral loads, *J Immunol* 170:477-86.
23. Garmashova, N., S. Atasheva, W. Kang, S. C. Weaver, E. Frolova, and I. Frolov. 2007. Analysis of Venezuelan equine encephalitis virus capsid protein function in the inhibition of cellular transcription. *J Virol* 81:13552-65.
24. Garmashova, N., R. Gorchakov, E. Volkova, S. Paessler, E. Frolova, and I. Frolov. 2007. The Old World and New World alphaviruses use different virus-specific proteins for induction of transcriptional shutoff. *J Virol* 81:2472-84.
25. Gorchakov, R., R. Hardy, C. M. Rice, and I. Frolov. 2004. Selection of functional 5' cis-acting elements promoting efficient Sindbis virus genome replication. *J Virol* 78:61-75.
26. Griffin, D. E. 2001, Alphaviruses, pp. 917-962. In D. M. Knipe and P. M. Howley (ed.), *Fields' Virology*, Fourth Edition. Lippincott, Williams and Wilkins, New York.
27. Harrington, L. E., K. M. Janowski, J. R. Oliver, A. J. Zajac, and C. T. Weaver. 2008. Memory CD4 T cells emerge from effector T-cell progenitors. *Nature* 452:356-60.
28. Hunt, A. R., S. Frederickson, T. Maruyama, J. T. Roehrig, and C. D. Blair. The first human epitope map of the alphaviral E1 and E2 proteins reveals a new E2 epitope with significant virus neutralizing activity. *PLoS Negl Trop Dis* 4:e739.
29. Jose, J., J. E. Snyder, and R. J. Kuhn. 2009. A structural and functional perspective of alphavirus replication and assembly. *Future Microbiol* 4:837-56.
30. Khanolkar, A., M. J. Fuller, and A. J. Zajac. 2004. CD4 T cell-dependent CD8 T, cell maturation. *J Immunol* 172:2834-44.
31. Kinney, R. M., J. J. Esposito, B. J. Johnson, J. T. Roehrig, J. H. Mathews, A. D. Barrett, and D. W. Trent. 1988.

31. Recombinant vaccinia/Venezuelan equine encephalitis (VEE) virus expresses VEE structural proteins. *J Gen Virol* 69 (Pt 12):3005-13.
32. Kinney, R. M., J. J. Esposito, J. H. Mathews, B. J. Johnson, J. T. Roehrig, A. D. Barrett, and D. W. Trent. 1988. Recombinant vaccinia virus/Venezuelan equine encephalitis (VEE) virus protects mice from peripheral VEE virus challenge. *J Virol* 62:4697-702.
33. Kinney, R. M., B. J. B. Johnson, J. B. Welch, K. R. Tsuchiya, and D. W. Trent. 1989. The full-length nucleotide sequences of the virulent Trinidad donkey strain of Venezuelan equine encephalitis virus and its attenuated vaccine derivative, strain TC-83. *Virology* 170:19-30.
34. Kulasegaran-Shylini, R., S. Atasheva, D. G. Gorenstein, and I. Frolov. 2009. Structural and functional elements of the promoter encoded by the 5' untranslated region of the Venezuelan equine encephalitis virus genome. *J Virol* 83:8327-39.
35. Kulasegaran-Shylini, R., V. Thiviyanathan, D. G. Gorenstein, and I. Frolov. 2009. The 5'UTR-specific mutation in VEEV TC-83 genome has a strong effect on RNA replication and subgenomic RNA synthesis, but not on translation of the encoded proteins. *Virology* 387:211-21.
36. Lauring, A. S., J. O. Jones, and R. Andino. Rationalizing the development of live attenuated virus vaccines. *Nat Biotechnol* 28:573-9.
37. Levis, R., B. G. Weiss, M. Tsiang, H. Huang, and S. Schlesinger. 1986, Deletion mapping of Sindbis virus DI RNAs derived from cDNAs defines the sequences essential for replication and packaging. *Cell* 44:137-145.
38. Mason, P. W., A. V. Shustov, and I. Frolov. 2006. Production and characterization of vaccines based on flaviviruses defective in replication. *Virology* 351:432-43.
39. Michel, G., O. Petrakova, S. Atasheva, and I. Frolov. 2007. Adaptation of Venezuelan equine encephalitis virus lacking 51-nt conserved sequence element to replication in mammalian and mosquito cells. *Virology* 362:475-87.
40. Monroe, S. S., J.-H. Ou, C. M. Rice, S. Schlesinger, E. G. Strauss, and J. H. Strauss. 1982. Sequence analysis of cDNAs derived from Sindbis virions and of defective interfering particles. *J. Virol.* 41:153-162.
41. Monroe, S. S., and S. Schlesinger. 1984, Common and distinct regions of defective-interfering RNAs of Sindbis virus. *J. Virol.* 49:865-872.
42. Monroe, S. S., and S. Schlesinger. 1983. RNAs from two independently isolated defective interfering particles of Sindbis virus contain a cellular tRNA sequence at their 5' ends. *Proc. Natl. Acad. Sci. USA* 80:3279-3283.
43. Mueller, S., D. Papamichail, J. R. Coleman, S. Skiena, and E. Wimmer, 2006. Reduction of the rate of poliovirus protein synthesis through large-scale codon deoptimization causes attenuation of viral virulence by lowering specific infectivity. *J Virol* 80:9687-96.
44. Owen, K. E., and R. J. Kuhn. 1997. Alphavirus budding is dependent on the interaction between the nucleocapsid and hydrophobic amino acids on the cytoplasmic domain of the E2 envelope glycoprotein. *Virology* 230:187-96.
45. Paessler, S., R. Z. Fayzulin, M. Anishchenko, I. P. Greene, S. C. Weaver, and I. Frolov, 2003. Recombinant Sindbis/Venezuelan equine encephalitis virus is highly attenuated and immunogenic. *J Virol* 77:9278-86.
46. Paessler, S., H. Ni, O. Petrakova, R. Z. Fayzulin, N. Yun, M. Anishchenko, S. C. Weaver, and I. Frolov. 2006. Replication and clearance of Venezuelan equine encephalitis virus from the brains of animals vaccinated with chimeric SIN/VEE viruses. *J Virol* 80:2784-96.
47. Pedersen, C. E., Jr., D. M. Robinson, and F. E. Cole, Jr. 1972, Isolation of the vaccine strain of Venezuelan equine encephalomyelitis virus from mosquitoes in Louisiana. *Am J Epidemiol* 95:490-6.
48. Perera, R., C. Navaratnarajah, and R. J. Kuhn. 2003. A heterologous coiled coil can substitute for helix I of the Sindbis virus capsid protein. *J Virol* 77:8345-53.
49. Perera, R., K. E. Owen, T. L. Tellinghuisen, A. E. Gorbalenya, and R. J. Kuhn. 2001. Alphavirus nucleocapsid protein contains a putative coiled coil alpha-helix important for core assembly. *J Virol* 75:1-10,
50. Pittman, P. R., R. S. Makuch, J. A. Mangiafico, T. L. Cannon, P. H. Gibbs, and C. J. Peters. 1996. Long-term duration of detectable neutralizing antibodies after administration of live-attenuated VEE vaccine and following booster vaccination with inactivated VEE vaccine. *Vaccine* 14:337-43.
51. Reed, D. S., T. Larsen, L. J. Sullivan, C. M. Lind, M. G. Lackemeyer, W. D. Pratt, and M. D. Parker. 2005. Aerosol exposure to western equine encephalitis virus causes fever and encephalitis in cynomolgus macaques. *J Infect Dis* 192:1173-82.
52. Reisen, W. K. 2001. Western equine encephalitis, p. 558-563. In M. W. Service (ed.), *The Encyclopedia of Arthropod-transmitted Infections*, CAB International, Wallingford, UK.
53. Rico-Hesse, R., S. C. Weaver, J. de Siger, G. Medina, and R. A. Salas. 1995. Emergence of a new epidemic/epizootic Venezuelan equine encephalitis virus in South America. *Proc. Natl. Acad. Sci. USA* 92:5278-5281.
54. Schlesinger, S., and M. J. Schlesinger (ed.). 1986, *The Togaviridae and Flaviviridae*. Plenum Press, New York.
55. Shustov, A. V., and I. Frolov. Efficient, trans-complementing packaging systems for chimeric, pseudoinfectious dengue 2/yellow fever viruses. *Virology* 400:8-17.
56. Shustov, A. V., P. W. Mason, and I. Frolov. 2007. Production of pseudoinfectious yellow fever virus with a two-component genome. *J Virol* 81:11737-48.
57. Strauss, J. H., and E. G. Strauss. 1994. The alphaviruses: gene expression, replication, evolution. *Microbiol. Rev.* 58:491-562.
58. Sviatchenko, V. A., E. V. Agapov, I. Urmanov, O. I. Serpinskii, I. V. Frolov, A. A. Kolykhalov, A. B. Ryzhikov, and S. V. Netesov. 1993. [The immunogenic properties of a recombinant vaccinia virus with an incorporated DNA copy of the 26S RNA of the Venezuelan equine encephalomyelitis virus]. *Vopr Virusol* 38:222-6.
59. Tellinghuisen, T. L., R. Perera, and R. J. Kuhn. 2001. In vitro assembly of Sindbis virus core-like particles from cross-linked dimers of truncated and mutant capsid proteins. *J Virol* 75:2810-7.
60. Vignuzzi, M., E. Wendt, and R. Andino. 2008. Engineering attenuated virus vaccines by controlling replication fidelity. *Nat Med* 14:154-61.
61. Volkova, E., E. Frolova, J. R. Darwin, N. L. Forrester, S. C. Weaver, and I. Frolov. 2008. IRES-dependent replication of Venezuelan equine encephalitis virus makes it highly attenuated and incapable of replicating in mosquito cells. *Virology* 377:160-9.
62. Volkova, E., R. Gorchakov, and I. Frolov. 2006. The efficient packaging of Venezuelan equine encephalitis virus-specific RNAs into viral particles is determined by nsP1-3 synthesis. *Virology* 344:315-27.
63. Wang, E., O. Petrakova, A. P. Adams, P. V. Aguilar, W. Kang, S. Paessler, S. M. Volk, I. Frolov, and S. C. Weaver.

2007. Chimeric Sindbis/eastern equine encephalitis vaccine candidates are highly attenuated and immunogenic in mice. *Vaccine* 25:7573-81.
64. Wang, E., E. Volkova, A. P. Adams, N. Forrester, S. Y. Xiao, I. Frolov, and S. C. Weaver. 2008. Chimeric alphavirus vaccine candidates for chikungunya. *Vaccine* 26:5030-5039.
65. Warrier, R., B. R. Linger, B. L. Golden, and R. J. Kuhn. 2008. Role of Sindbis virus capsid protein region II in nucleocapsid core assembly and encapsidation of genomic RNA, *J Virol* 82:4461-70.
66. Weaver, S. C. 2001. Eastern equine encephalitis, p. 151-159. In M. W. Service (ed.), *The Encyclopedia of Arthropod-transmitted Infections*. CAB International, Wallingford, UK.
67. Weaver, S. C. 2001. Venezuelan equine encephalitis, p. 539-548. In M. W. Service (ed.), *The Encyclopedia of Arthropod-transmitted Infections*. CAB International, Wallingford, UK,
68. Weaver, S. C., and A. D. Barrett. 2004. Transmission cycles, host range, evolution and emergence of arboviral disease. *Nat Rev Microbiol* 2:789-801.
69. Weaver, S. C., A. Hagenbaugh, L. A. Bellew, L. Gousset, V. Mallampalli, J. J. Holland, and T. W. Scott. 1994, Evolution of alphaviruses in the eastern equine encephalomyelitis complex. *J Virol* 68:158-69.
70. Weaver, S. C., R. Salas, R. Rico-Hesse, G. V. Ludwig, M. S. Oberste, J. Boshell, and R. B. Tesh. 1996. Re-emergence of epidemic Venezuelan equine encephalomyelitis in South America. VEE Study Group. *Lancet* 348:436-40.
71. Weiss, B., U. Geigenmuller-Gnirke, and S. Schlesinger. 1994. Interactions between Sindbis virus RNAs and a 68 amino acid derivative of the viral capsid protein further defines the capsid binding site. *Nucleic Acids Res.* 22:780-6.
72. Weiss, B., H. Nitschko, I. Ghattas, R. Wright, and S. Schlesinger. 1989. Evidence for specificity in the encapsidation of Sindbis virus RNAs. *J. Virol.* 63:5310-5318.
73. Weiss, B., R. Rosenthal, and S. Schlesinger. 1980. Establishment and maintenance of persistent infection by Sindbis virus in BHK cells. *J. Virol.* 33:463-474.
74. Widman, D. G., I. Frolov, and P. W. Mason. 2008. Third-generation flavivirus vaccines based on single-cycle, encapsidation-defective viruses. *Adv Virus Res* 72:77-126.
75. Wimmer, E., S. Mueller, T. M. Tumpey, and J. K. Taubenberger. 2009. Synthetic viruses: a new opportunity to understand and prevent viral disease. *Nat Biotechnol* 27:1163-72.
76. Yi, J. S., M. Du, and A. J. Zajac. 2009. A vital role for interleukin-21 in the control of a chronic viral infection. *Science* 324:1572-6.
77. Zhang, W., M. Heil, R. J. Kuhn, and T. S. Baker. 2005. Heparin binding sites on Ross River virus revealed by electron cryo-microscopy. *Virology* 332:511-8,
78. Zuker, M. 2003. Mfold web server for nucleic acid folding and hybridization prediction. *Nucleic Acids Res* 31:3406-15.
79. Zuker, M., D. H. Mathews, and D. H. Turner. 1999. *Algorithms and thermodynamics for RNA secondary structure prediction: A practical guide*. Kluwer Academic Publishers.

---

What is claimed is:

1. A pseudoinfectious alphavirus genome encoding: a) alphavirus nonstructural proteins nsP1-4,
   b) alphavirus structural proteins E2 and E1, and
   c) a Venezuelan equine encephalitis virus (VEEV) capsid protein comprising the amino acid sequence of SEQ ID NO:2 in which two or more amino acids are substituted, resulting in a phenotype of diminished or eliminated packaging of viral genetic material into an alphavirus particle comprising said alphavirus capsid protein, and wherein the amino acid substitutions change two or more positively charged amino acids selected from R16; R23; R24: R29; R53; R54; K64; K65; K67; K68: K73; K75; K81; K82; K83: K84: K88: K89: K90; K92: K99: K105: K106; K107; K110; and/or K111, in any combination, to neutral or negatively charged amino acids.

2. A pseudoinfectious alphavirus particle comprising the pseudoinfectious alphavirus genome of claim 1.

3. The pseudoinfectious alphavirus particle of claim 2, wherein the capsid protein comprises a substitution selected from the group consisting of:
   1) R16G;
   2) R23A;
   3) R24N;
   4) R29G;
   5) R53N;
   6) R54N;
   7) K64S;
   8) K65N;
   9) K67G;
   10) K68N;
   11) K73A;
   12) K75N;
   13) K81S;
   14) K82G;
   15) K83N;
   16) K84N;
   17) K88G;
   18) K89G;
   19) K9ON;
   20) K92S;
   21) K99N;
   22) K105G;
   23) K106N;
   24) K107S;
   25) K110A;
   26) K111S; and
   27) any combination of (1) through (26) above.

4. A population of alphavirus particles, comprising the pseudoinfectious alphavirus particle of claim 2.

5. A pharmaceutical composition comprising the pseudoinfectious alphavirus particle of claim 2 in a pharmaceutically acceptable carrier.

6. A method of eliciting or enhancing an immune response to an alphavirus in a subject, comprising administering to the subject an effective amount of the pseudoinfectious alphavirus particle of claim 2, thereby eliciting or enhancing an immune response to an alphavirus in the subject.

7. A method of treating and/or inhibiting an alphavirus infection in a subject, comprising administering to the subject an effective amount of the pseudoinfectious alphavirus particle of claim 2, thereby treating and/or inhibiting an alphavirus infection in the subject.

8. A method of producing pseudoinfectious alphavirus particles in cell culture, comprising introducing into an isolated cell:
   a) the pseudoinfectious alphavirus genome of claim 1; and
   b) a helper nucleic acid molecule encoding alphavirus RNA-binding competent capsid protein; and
maintaining the cell in culture to produce the pseudoinfectious alphavirus particles.

9. A method of producing pseudoinfectious alphavirus particles in cell culture, comprising introducing the pseudoinfectious alphavirus genome of claim 1 into an isolated cell containing a nucleic acid molecule encoding an alphavirus RNA-binding competent capsid protein; and
maintaining the cell in culture to produce the pseudoinfectious alphavirus particles.

10. A population of alphavirus particles comprising the pseudoinfectious alphavirus particles produced by the method of claim 8.

11. A method of treating and/or inhibiting an alphavirus infection in a subject, comprising administering to the subject an effective amount of the population of pseudoinfectious alphavirus of claim 10, thereby treating and/or inhibiting an alphavirus infection in the subject.

* * * * *